(12) United States Patent
Zhao et al.

(10) Patent No.: US 12,269,808 B2
(45) Date of Patent: Apr. 8, 2025

(54) AMINO DITHIOPERACID THIOESTER COMPOUND, PREPARATION METHOD THEREFOR, AND USE THEREOF

(71) Applicants: FUDAN UNIVERSITY, Shanghai (CN); EAST CHINA NORMAL UNIVERSITY, Shanghai (CN)

(72) Inventors: Weili Zhao, Shanghai (CN); Xiongwen Zhang, Shanghai (CN); Xiaochun Dong, Shanghai (CN); Yiwei Li, Shanghai (CN); Shuang Xu, Shanghai (CN); Shanshan Lu, Shanghai (CN); Guangyu Lin, Shanghai (CN); Kedan Gu, Shanghai (CN)

(73) Assignees: FUDAN UNIVERSITY, Shanghai (CN); EAST CHINA NORMAL UNIVERSITY, Shanghai (CN)

( * ) Notice: Subject to any disclaimer, the term of this patent is extended or adjusted under 35 U.S.C. 154(b) by 420 days.

(21) Appl. No.: 17/786,159

(22) PCT Filed: Nov. 27, 2020

(86) PCT No.: PCT/CN2020/132332
§ 371 (c)(1),
(2) Date: Jun. 16, 2022

(87) PCT Pub. No.: WO2021/121012
PCT Pub. Date: Jun. 24, 2021

(65) Prior Publication Data
US 2022/0396557 A1    Dec. 15, 2022

(30) Foreign Application Priority Data
Dec. 19, 2019  (CN) .......................... 201911318067.9
Oct. 15, 2020  (CN) .......................... 202011100806.X

(51) Int. Cl.
| | |
|---|---|
| C07D 295/21 | (2006.01) |
| A61P 21/00 | (2006.01) |
| C07D 205/04 | (2006.01) |
| C07D 207/12 | (2006.01) |
| C07D 207/16 | (2006.01) |
| C07D 209/08 | (2006.01) |
| C07D 209/44 | (2006.01) |
| C07D 295/194 | (2006.01) |
| C07D 295/195 | (2006.01) |
| C07D 491/107 | (2006.01) |

(52) U.S. Cl.
CPC ............ C07D 295/21 (2013.01); A61P 21/00 (2018.01); C07D 205/04 (2013.01); C07D 207/12 (2013.01); C07D 207/16 (2013.01); C07D 209/08 (2013.01); C07D 209/44 (2013.01); C07D 295/194 (2013.01); C07D 295/195 (2013.01); C07D 491/107 (2013.01)

(58) Field of Classification Search
CPC .. C07D 207/16; C07D 209/08; C07D 209/44; C07D 295/194; C07D 295/195; C07D 491/107
See application file for complete search history.

(56) References Cited

U.S. PATENT DOCUMENTS

| | | | |
|---|---|---|---|
| 3,810,890 A | | 5/1974 | Dunbar et al. |
| 3,954,746 A | * | 5/1976 | Dunbar ................ C07D 295/20 544/85 |
| 2013/0123266 A1 | | 5/2013 | Zagury et al. |
| 2016/0175401 A1 | | 6/2016 | Spiegelman et al. |

OTHER PUBLICATIONS

International Search Report of Application No. PCT/CN2020/132332 mailed Mar. 3, 2021, 4 pages.

* cited by examiner

*Primary Examiner* — Laura L Stockton
(74) *Attorney, Agent, or Firm* — Ware, Fressola, Maguire & Barber LLP

(57) ABSTRACT

An amino dithioperacid thioester compound, a preparation method therefor, and use thereof. The structural formula of compound is as shown in formula I: wherein m=1-11, X is a nitrogen-containing aliphatic heterocyclic ring, and a nitrogen atom in the aliphatic heterocyclic ring is connected to a carbon atom of a thiocarbonyl group. The compounds disclosed by the invention are found to be capable of relieving muscular atrophy and lipolysis caused by cancer cachexia through in-vivo and in-vitro experiments. The compounds are also capable of obviously relieving weight and food intake reduction caused by cancer cachexia in animal experiments, so that the carbamo(dithioperoxo)thioates compounds have the effect on resisting cancer cachexia, can be applied to the treatment of cancer cachexia and related diseases, and become one kind of ideal cancer cachexia treatment medicament.

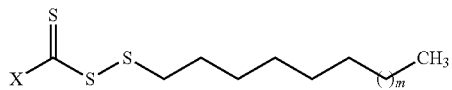

8 Claims, 11 Drawing Sheets

DRAWINGS

CT

C26 medium

C26+1 (25µM)

C26+1 (50µM)

C26+1 (100µM)

C26+2 (12.5µM)

C26+2 (25µM)

C26+2 (50µM)

C26+3 (25µM)

C26+3 (50µM)

C26+3 (100µM)

C26+4 (3.125µM)

C26+4 (6.25µM)

C26+4 (12.5µM)

C26+5 (25µM)

C26+5 (50µM)

C26+6 (25µM)

C26+6 (50µM)

C26+6 (100µM)

C26+7 (25µM)

C26+7 (50µM)

C26+7 (100µM)

C26+8 (25µM)

C26+8 (50µM)

C26+8 (100µM)

C26+9 (25µM)

C26+9 (50µM)

C26+9 (100µM)

C26+10 (25µM)

C26+10 (50µM)

C26+10 (100µM)

C26+11 (25µM)

C26+11 (50µM)

C26+12 (25µM)

C26+12 (50µM)

C26+12 (100µM)

C26+13 (25µM)

C26+13 (50µM)

C26+14 (25µM)

C26+14 (50µM)

C26+15 (25μM)

C26+15 (50μM)

C26+16 (25μM)

C26+16 (50μM)

C26+17 (25μM)

C26+17 (50μM)

AMINO DITHIOPERACID THIOESTER COMPOUND, PREPARATION METHOD THEREFOR, AND USE THEREOF

TECHNICAL FIELD

The present invention belongs to the field of medicinal chemistry, which is about the carbamo(dithioperoxo)thioate compounds and their pharmaceutical uses, especially the preparation of carbamo(dithioperoxo)thioate compounds with nitrogen-containing aliphatic heterocyclic ring and their application in the treatment of cachexia.

BACKGROUND OF THE INVENTION

Cachexia is a progressive wasting syndrome, characterized by weight loss, anemia, mental depression and other systemic failures, primarily caused by cancer and other serious chronic diseases (such as chronic pulmonary obstruction, chronic heart failure, AIDS, etc.). Cachexia caused by tumors is called cancer cachexia. Cancer cachexia is a major complication of various malignant tumors and the main cause of death in many cancer patients. The prevention and treatment of cancer cachexia has become an increasingly important part of multidisciplinary comprehensive treatment of malignant tumors, which is receiving more and more attention. Cancer cachexia is a wasting syndrome marked by systemic metabolic disorders, progressive muscle and fat wasting, weight loss, and progressive systemic organ failure caused by tumor cells' products and cytokines released by the body. The most important feature of cancer cachexia is the significant weight loss of patients caused by skeletal muscle atrophy. Cancer cachexia affects 50% to 80% of advanced tumor patients, with 40% of breast cancer and leukemia patients. 50% of lung cancer, colon cancer and prostate cancer patients and 80% of gastric cancer and pancreatic cancer patients suffering from it. About 20% of tumor patients die directly from cardiopulmonary failure caused by cachexia, as a result, making cancer cachexia the leading cause of death in many tumor patients. Cancer cachexia not only reduces the effectiveness of chemotherapy and radiotherapy and shortens the survival time, but also has a serious negative impact on patient survival quality.

Cancer cachexia has a complicated pathophysiology, and there is no effective treatment. At present, there are no anti-cancer cachexia drugs in the market and the only strategy to prevent cancer cachexia from worsening in clinical practice is to increase patients' nutritional intake. To increase body weight, stimulate appetite and overcome cancer cachexia, current clinical treatment focuses on nutritional support, appetite stimulation, suppression of inflammatory factors and cytokines. Omega-3 fatty acids, for example, have been used as nutritional supplements in clinical investigations of weight loss during cancer cachexia in patients with head and neck cancer, but they did not significantly enhance patient weight and survival time. Progestins like megestrol and medroxyprogesterone are commonly used in appetite stimulating hormone therapy, and they can be paired with ghrelin and omega-3 fatty acids. These palliative therapy regiments have improved clinical effects in patients with cancer cachexia, but they are still difficult to achieve effective therapeutic outcomes. Researchers have also investigated a range of anti-inflammatory cytokine antibodies, such as specific antibodies to IL-1α, IL-6, TNF-α, myostatin and other factors, but it was shown that inhibiting one of these factors was not enough to halt cachexia from developing. Infliximab (monoclonal antibody to TNFα) and Clazakizumab (monoclonal antibody to IL-6) were not shown to significantly improve weight loss, skeletal muscle atrophy and quality of life in patients with pancreatic cancer cachexia and non-small cell lung cancer cachexia, respectively. In addition, ghrelin receptor agonists, selective androgen receptor (AR) agonists, adrenergic β-blockers and anti-myostatin peptides are all hot research subjects. In near future, anamorelin (a ghrelin receptor agonist) and enobosarm (a selective androgen receptor agonist) were the most promising new drugs in clinical trials. However, phase III clinical trials for both drugs are currently unsatisfactory.

In conclusion, cancer cachexia is a common complication in patients with various malignant tumors, which not only reduces the efficacy of chemotherapy and radiotherapy and shortens life time, but also has a serious negative impact on survival quality of patients. Despite widespread agreement on the importance of cancer cachexia treatment, there has been no breakthrough in the development of therapeutic methods and new drugs for cancer cachexia, and clinical treatment effectiveness is limited, and no drug has been approved to be used as a specific drug for cancer cachexia for marketing, due to much unknown pathophysiology of cancer cachexia. As a result, developing new anti-cancer cachexia medicines with the independent intellectual property rights is a critical scientific and technological challenge that must be urgently addressed and it will certainly bring great social and economic benefits.

SUMMARY OF THE INVENTION

The technological problem addressed by the present invention is that there is no breakthrough in the development of therapeutic methods and new drug for cancer cachexia, that clinical treatment effectiveness is limited and that no drug has been approved to be used as a specific drug for cancer cachexia for marketing. The present invention designs, synthesizes and studies the novel anti-cancer cachexia compounds, develops new anti-cancer cachexia drugs with the autonomous independent intellectual property rights, and addresses critical scientific and technological challenges urgently needed for cancer treatment.

The purpose of the present invention is to provide the novel carbamo(dithioperoxo)thioate compounds for oral administration that have a significant anti-cachexia effect in various tissues by affecting various signaling pathways to alleviate the process of skeletal muscle atrophy and fat degradation in cancer cachexia. The findings of the experiments revealed that the compounds presented have good anti-cachexia activity when taken orally and can be further developed into the innovative anti-cachexia medicines.

In order to improve the above drawbacks and defects of existing technology, the present invention provides a series of carbamo(dithioperoxo)thioate compounds with nitrogen-containing aliphatic heterocyclic ring. These compounds can be used in the treatment of cachexia, especially solid tumor caused cancer cachexia.

The present invention relates to following technical solutions.

The carbamo(dithioperoxo)thioate compound represented by formula I, or its pharmaceutically acceptable salts, wherein the formula I is:

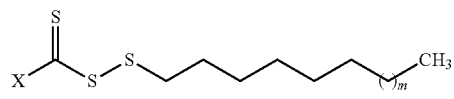

I

Wherein.

m=1-11, preferably, m=1-9; X is a nitrogen-containing aliphatic heterocyclic ring and the nitrogen atom in the aliphatic heterocyclic ring is connected to the carbon atom of the thiocarbonyl group.

Preferably, the above carbamo(dithioperoxo)thioate compound or its pharmaceutically acceptable salts, wherein, m=3-5, preferably, m=5.

Preferably, the above carbamo(dithioperoxo)thioate compound or its pharmaceutically acceptable salts, wherein, the aliphatic heterocyclic ring may contain oxygen atom.

Preferably, the above carbamo(dithioperoxo)thioate compound or its pharmaceutically acceptable salts, wherein, the number of nitrogen atoms is 1-2.

Preferably, the above carbamo(dithioperoxo)thioate compound or its pharmaceutically acceptable salts, wherein, the nitrogen-containing aliphatic heterocycle is selected from saturated monocyclic aliphatic heterocycle, fused or spiro derivative of saturated monocyclic aliphatic heterocycle.

Preferably, the above carbamo(dithioperoxo)thioate compound or its pharmaceutically acceptable salts, wherein the saturated nitrogen-containing monocyclic aliphatic heterocycle is 4-7 membered heterocycle; preferably, saturated nitrogen-containing monocyclic aliphatic heterocycle is 4-6 membered heterocycle.

Preferably, the above carbamo(dithioperoxo)thioate compound or its pharmaceutically acceptable salts, wherein the saturated nitrogen-containing monocyclic aliphatic heterocycle contains five to six atoms. Further preferably, wherein the saturated nitrogen-containing monocyclic aliphatic heterocycle contains five atoms.

Preferably, the above carbamo(dithioperoxo)thioate compound or its pharmaceutically acceptable salts, wherein the saturated nitrogen-containing monocyclic aliphatic heterocycle is selected from pyrrolidine, substituted pyrrolidine, piperidine, morpholine, azetidine, piperazine. Further preferably, nitrogen-containing aliphatic heterocyclic ring is pyrrolidine.

Preferably, the above carbamo(dithioperoxo)thioate compound or its pharmaceutically acceptable salts, wherein the ring which connected with a saturated nitrogen-containing monocyclic aliphatic heterocycle to form a fused-ring heterocycle or spirocycle contains four to six atoms.

Preferably, the above carbamo(dithioperoxo)thioate compound or its pharmaceutically acceptable salts, wherein the ring which connected to the saturated nitrogen-containing monocyclic aliphatic heterocycle to form a fused-ring heterocycle or spirocycle is selected from any one of the following:

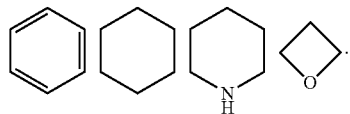

Preferably, the above carbamo(dithioperoxo)thioate compound or its pharmaceutically acceptable salts, wherein the nitrogen-containing aliphatic heterocyclic ring may contain substituent group. The substituent group is selected from hydroxy group. C1-4 alkyl group.

Preferably, the above carbamo(dithioperoxo)thioate compound or its pharmaceutically acceptable salts, wherein the nitrogen-containing aliphatic heterocyclic ring is selected from pyrrolidine, substituted pyrrolidine, piperidine, morpholine, azetidine, piperazine, indoline, isoindolin, octahydro-1H-indole, octahydro-1H-isoindole, 2-oxa-6-azaspiro[3.4]octane.

Preferably, the substituent group on pyrrolidine is selected from hydroxy group. C1-4 alkyl group.

Preferably, the nitrogen-containing aliphatic heterocyclic ring is selected from pyrrolidine, octahydro-1H-isoindole, azetidine, 2-oxa-6-azaspiro[3.4]octane; preferably, nitrogen-containing aliphatic heterocyclic ring is pyrrolidine.

Preferably, the above carbamo(dithioperoxo)thioate compound or its pharmaceutically acceptable salts, wherein said compound is selected from the following compounds or the derivatives of the following compounds in which the nitrogen-containing aliphatic heterocyclic ring may contain substituent group.

(1)

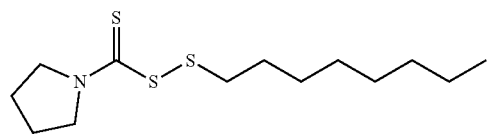 [SMILES: CCCCCCCCSSC(=S)N1CCCC1]

(2)

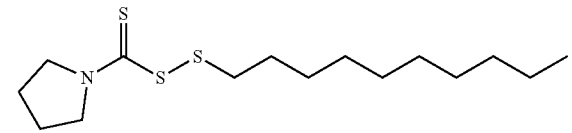 [SMILES: CCCCCCCCCCSSC(=S)N1CCCC1]

(3)

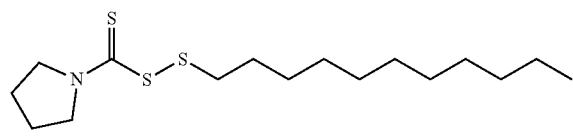 [SMILES: CCCCCCCCCCCSSC(=S)N1CCCC1]

(4)

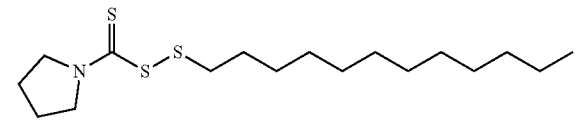 [SMILES: CCCCCCCCCCCCSSC(=S)N1CCCC1]

(5)

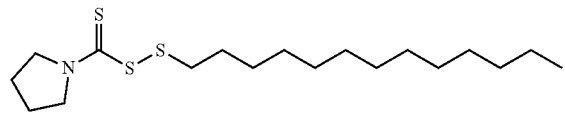 [SMILES: CCCCCCCCCCCCCSSC(=S)N1CCCC1]

(6)

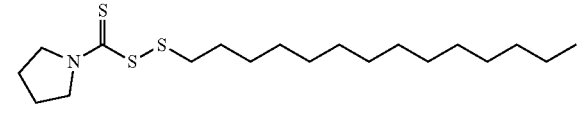 [SMILES: CCCCCCCCCCCCCCSSC(=S)N1CCCC1]

(7)

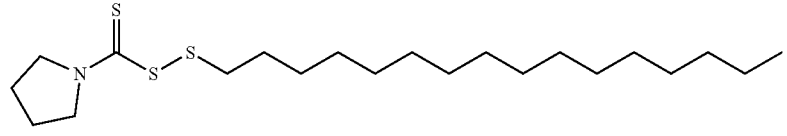

-continued

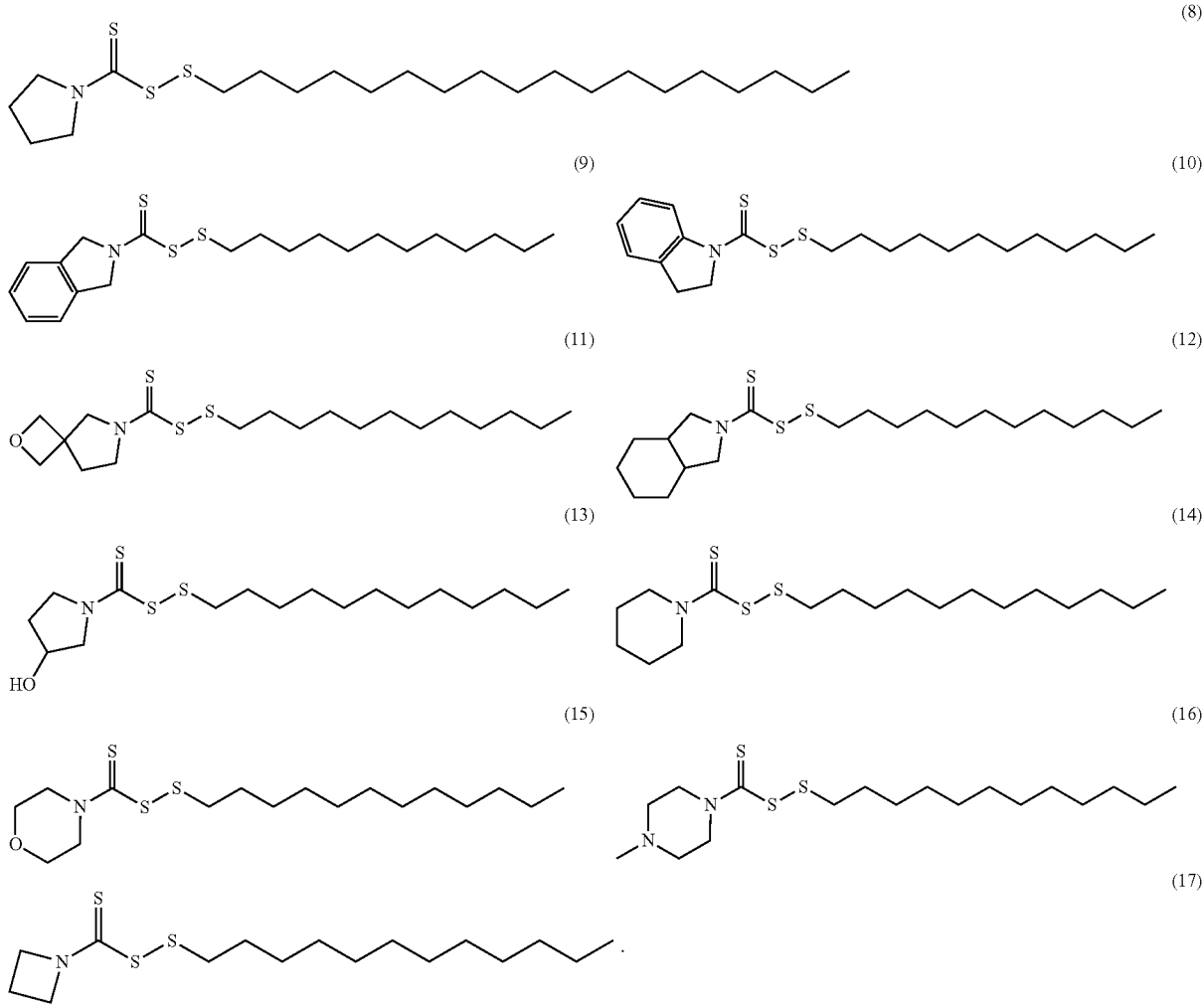

Preferably, the substituent group is selected from hydroxy group, C1-8 alkyl group. Further preferably, the substituent group is selected from hydroxy group, C1-4 alkyl group.

The present invention also provides a preparation method of carbamo(dithioperoxo)thioate compound or its pharmaceutically acceptable salt thereof, characterized in that, comprising the following steps:

(1) Add the compound described in formula II to the nitrogen-containing aliphatic heterocyclic compound, and then add carbon disulfide and triethylamine with stirring;

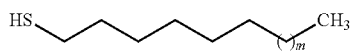

II (2) Add carbon tetrabromide with stirring:
(3) After the reaction, the carbamo(dithioperoxo)thioate compound or a pharmaceutically acceptable salt thereof is obtained.

Preferably, in the above preparation method, the molar ratio of the compound containing an aliphatic heterocycle to the compound of formula II is 1: (0.5-1.5);

The molar ratio of the compound containing aliphatic heterocycle to carbon disulfide is 1: (0.5-1.5);

The molar ratio of the compound containing aliphatic heterocycle to triethylamine is 1: (0.5-1.5);

The molar ratio of the compound containing aliphatic heterocycle to carbon tetrabromide is 1: (1.5-2.5)

Preferably, in the above preparation method, the processes in steps (1) and (2) are carried out under ice bath conditions, and the reaction process in step (3) is at room temperature.

Preferably, in the above preparation method, the step (1) is performed in an organic solvent, and the organic solvent is preferably dichloromethane or tetrahydrofuran.

Preferably, in the above preparation method, the product obtained after the reaction in step (3) needs to be washed with water, saturated sodium chloride aqueous solution and dried over anhydrous sodium sulfate.

Preferably, in the preparation method, the reaction time of step (3) is 1-3 hours; preferably, the reaction process further includes the step of stirring, and the stirring rate is 800-1200 rpm.

Preferably, in the preparation method, after the reaction in step (3), a process of column chromatography is required, and the eluent used in the column chromatography includes petroleum ether and dichloromethane, and the volume ratio is (1-10):1: Alternatively, the eluent includes petroleum ether and ethyl acetate in a volume ratio of (3-25):1.

The present invention also provides a composition, which is characterized by comprising the above-mentioned carbamo(dithioperoxo)thioate compound or a pharmaceutically acceptable salt thereof, and a pharmaceutically acceptable additive, preferably, the additive comprises pharmaceutically acceptable carrier, diluent or excipient.

The present invention also provides the above-mentioned carbamo(dithioperoxo)thioate compounds or its pharmaceutically acceptable salts thereof, and the application of the above-mentioned composition in the preparation of anti-cachexia drugs, especially anti-cancer cachexia drugs.

In the present invention, the term "thiocarbonyl group" used herein refers to —CS—, the structure is shown as follow:

The term "carbamo(dithioperoxo)thioate" refers to compound containing three sulfur atoms, the structure is shown as follow:

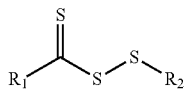

As used herein, the term "cyclic compound" refers to a carbocyclic compound or a heterocyclic compound. A carbocyclic compound refers to an aliphatic cyclic compound or an aromatic cyclic compound, and a heterocyclic compound refers to an aliphatic heterocycle or aromatic heterocycle.

The term "heterocycle" as used herein refers to an organic compound containing a heterocyclic structure in the molecule. The atoms constituting the ring contain at least one heteroatom, such as nitrogen atom, sulfur atom, and oxygen atom, in addition to carbon atoms. And the heterocycle may contain one ring, two rings, or multiple rings.

The term "aliphatic cyclic compound" as used herein refers to cyclic hydrocarbons and their derivatives formed by intramolecular condensation of chain hydrocarbons and their derivatives, including saturated cyclic hydrocarbons (also called saturated aliphatic rings) or unsaturated cyclic hydrocarbons (unsaturated alicyclic), saturated cyclic hydrocarbons such as cycloalkanes or cycloalkenes, preferably, saturated cyclic hydrocarbons or unsaturated cyclic hydrocarbons having three to seven carbon atoms and zero heteroatoms, saturated cyclic hydrocarbons such as cyclopropane, cyclobutane, cyclopentane or cyclohexane, etc.; unsaturated cyclic hydrocarbons such as cyclopropene, cyclobutene, cyclopentene, cyclohexene, cyclobutadiene, cyclopentadiene, etc. The alicyclic ring may be one ring, two rings or multiple rings.

The term "aromatic cyclic compound" as used herein refers to the aromatic molecule with a conjugated planar ring system and delocalized π electrons, such as benzene, benzene homologues, substituted benzene rings, fused rings aromatic hydrocarbons etc.

The term "aliphatic heterocycle" used herein, also known as alicyclic heterocycle, refers to a class of heterocyclic compounds without aromaticity, which may contain one ring, two rings or multiple rings. For bonds between atoms, it can be a single bond to form a saturated aliphatic heterocycle, or a double bond to form an unsaturated aliphatic heterocycle.

The term "aromatic heterocycle", corresponding to "aliphatic heterocycle", refers to a heterocyclic compound with aromaticity. Specifically, it refers to a molecule with delocalized a electrons for a fully conjugated, monocyclic, planar multi-double bond species.

The term "heterocyclic group" as used herein refers to a group formed after a heteroatom in a heterocyclic ring loses a hydrogen atom. For example, X linked to a thiocarbonyl group in claim 1 can also be referred to as a heterocyclic group.

As used herein, the term "heteroatom" refers to nitrogen, oxygen, sulfur atom.

The term "spirocycle" used in the present invention refers to a polycyclic organic compound formed by two or more carbocyclic or heterocyclic rings sharing one carbon atom. The carbon atom can be shared by benzene ring and benzene ring, shared by benzene ring and heterocycle, shared by benzene ring and aliphatic ring, shared by heterocycle and heterocycle, shared by heterocycle and aliphatic ring, shared by aliphatic ring and aliphatic ring.

The term "fused ring" used in the present invention refers to a polycyclic organic compound formed by two or more carbocyclic or heterocyclic rings sharing a ring edge. The ring edge can be shared of benzene ring and benzene ring, shared by benzene ring and heterocyclic ring, shared by benzene ring and aliphatic ring, shared by heterocyclic ring and heterocyclic ring, shared by heterocyclic ring and aliphatic ring, shared by aliphatic ring and aliphatic ring.

As used herein, the term "substituent group" refers to hydroxy group, carboxyl group, halo group, cyano group, alkyl ($C_{1-4}$ alkyl) group, alkoxy group, alkenyl group, aryl group, haloalkyl group, haloalkoxy group, heterocyclic alkyl group, heterocyclic carboxyl group, hydroxyalkyl group, nitro group, etc.

As used herein, the term "the compounds in present invention" refers to compound of Formula I and its pharmaceutically acceptable enantiomers, diastereoisomers or salts.

The compounds in the present invention may exist as pharmaceutically acceptable salts, in the form of water-soluble, oil-soluble or dispersible salts and zwitterions. "Pharmaceutically acceptable" means that during patient contact or use there is no undue toxicity, irritating reactions or complications, and has its intended use.

The composition in present invention may comprise compound of Formula I and its pharmaceutically acceptable salts, also may comprise one or two kinds of pharmaceutically acceptable carrier, diluent agent or excipient to form pharmaceutical formulation. Wherein, "pharmaceutically acceptable" refers to non-toxic, non-irritant, uncomplicated, and possess the intended usage during treatment on patients.

The composition in present invention comprise compound of Formula I and its pharmaceutically acceptable salts, also may comprise one or two kinds of pharmaceutically acceptable carrier, diluent agent or excipient to form pharmaceutical formulation. Wherein, "pharmaceutically acceptable" refers to non-toxic, non-irritant, uncomplicated, and possess the intended usage during treatment on patients.

The pharmaceutical formulations in the present invention can be tablets, capsules, fluids, powders or aerosols, etc., and can also include pharmaceutically inert carriers such as ethanol, glycerol, water, etc., if necessary, can also add suitable binders, corrective agents, flavoring agents, preservatives, dispersing agents or coloring agents, etc.

The pharmaceutical formulations in the present invention can be administered by any feasible route, and the administration modes include oral, rectal, nasal, topical (including buccal, sublingual or transdermal) routes.

As used herein, the term "room temperature" refers to 15-30° C.

Unless otherwise specified, the percentages used in the present invention are all mass percentages.

The following abbreviations will be used throughout the examples:

TLC: thin-layer chromatography, PE: petroleum ether, EA: ethyl acetate. Et$_3$N: triethyl amine. DCM: dichloromethane, Chloroform-d: deuterated chloroform, $^1$H NMR: nuclear magnetic resonance hydrogen spectrum, $^{13}$C NMR: nuclear magnetic resonance carbon spectrum, FBS: fetal bovine serum. HS: horse serum. DMEM: dulbecco's modified eagle medium, PBS buffer: phosphate buffered saline. DMSO: dimethyl sulfoxide, HE staining: hematoxylin-eosin staining.

The present invention has the following advantages: in in vitro and in vivo experiments, the compounds of the present invention have been found to alleviate muscle atrophy and fat lipolysis caused by cancer cachexia, and in animal experiments it was shown to significantly alleviate the decrease in body weight and food intake caused by cancer cachexia, indicating that carbamo(dithioperoxo)thioates compounds have anti-cancer cachexia effects and can be used to the treat cancer cachexia and its related diseases, which could be potential ideal drugs for treating cancer cachexia.

DETAILED METHODS AND EXAMPLES

Figure 1:
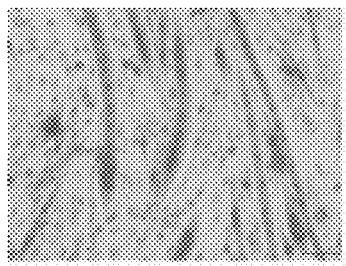
FIG. 1 shows the HE staining images of the control group in Example 18.
Figure 2:
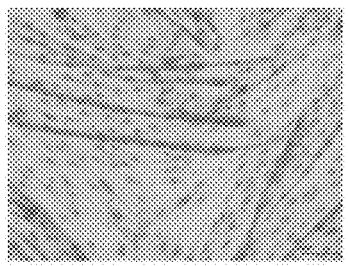
FIG. 2 shows the HE staining images of the model group in Example 18.
Figure 3:
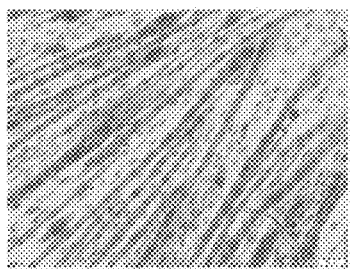
FIG. 3 shows the HE staining images of experimental group 1 in Example 18.
Figure 4:
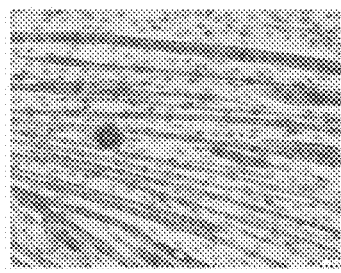
FIG. 4 shows the HE staining images of experimental group 2 in Example 18.
Figure 5:
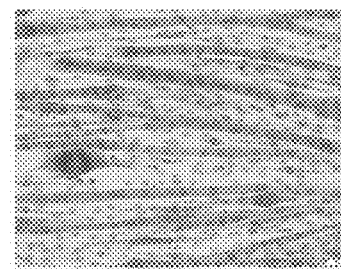
FIG. 5 shows the HE staining images of experimental group 3 in Example 18.
Figure 6:
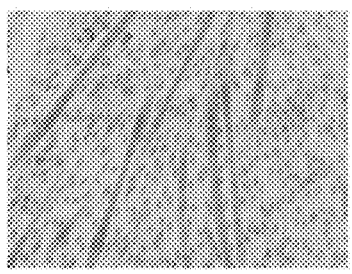
FIG. 6 shows the HE staining images of experimental group 4 in Example 18.
Figure 7:
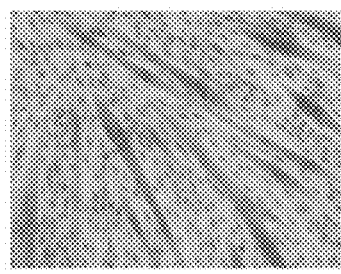
FIG. 7 shows the HE staining images of experimental group 5 in Example 18.
Figure 8:
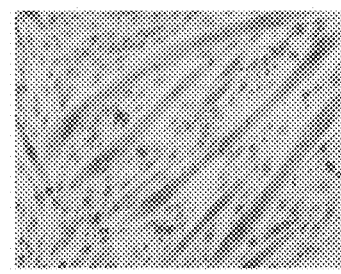
FIG. 8 shows the HE staining images of experimental group 6 in Example 18.
Figure 9:
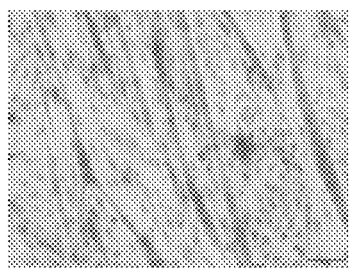
FIG. 9 shows the IE staining images of experimental group 7 in Example 18.
Figure 10:
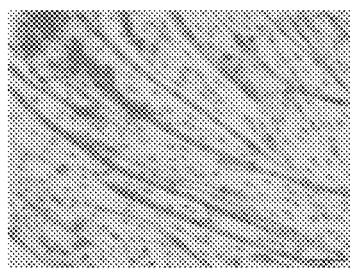
FIG. 10 shows the HE staining images of experimental group 8 in Example 18.
Figure 11:
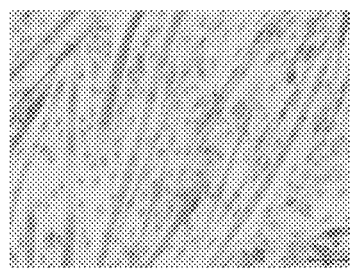
FIG. 11 shows the HE staining images of experimental group 9 in Example 18.
Figure 12:
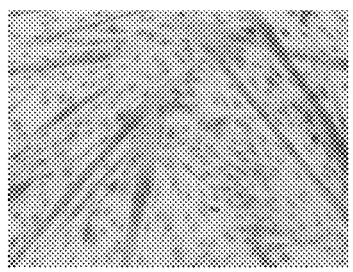
FIG. 12 shows the HE staining images of experimental group 10 in Example 18.
Figure 13:
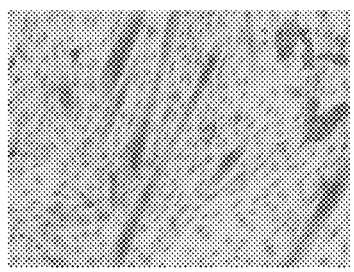
FIG. 13 shows the HE staining images of experimental group 11 in Example 18.
Figure 14:
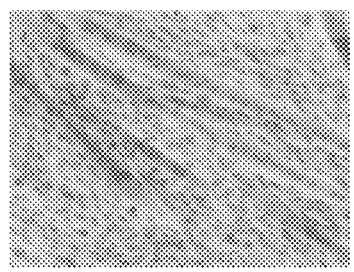
FIG. 14 shows the HE staining images of experimental group 12 in Example 18.
Figure 15:
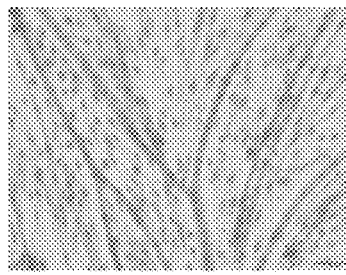
FIG. 15 shows the HE staining images of experimental group 13 in Example 18.
Figure 16:
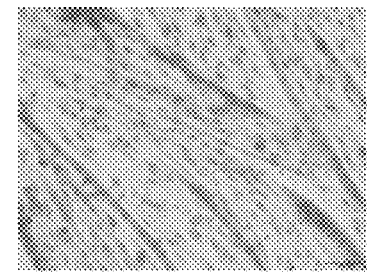
FIG. 16 shows the HE staining images of experimental group 14 in Example 18.
Figure 17:
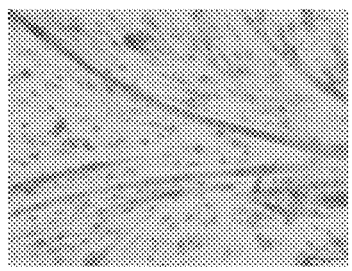
FIG. 17 shows the HE staining images of experimental group 15 in Example 18.
Figure 18:
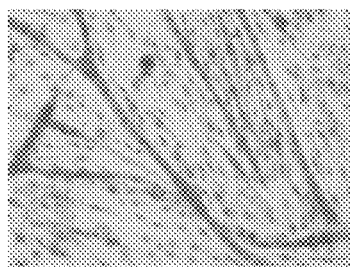
FIG. 18 shows the HE staining images of experimental group 16 in Example 18.
Figure 19:
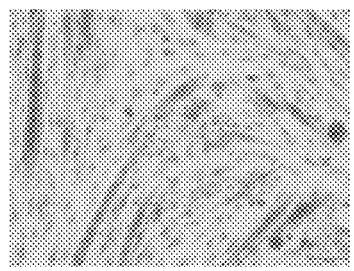
FIG. 19 shows the HE staining images of experimental group 17 in Example 18.
Figure 20:
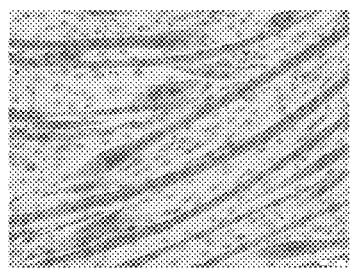
FIG. 20 shows the HE staining images of experimental group 18 in Example 18.
Figure 21:
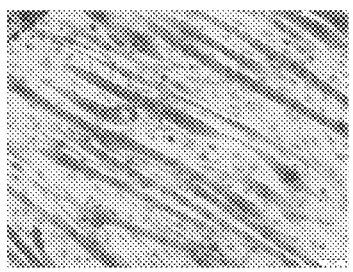
FIG. 21 shows the HE staining images of experimental group 19 in Example 18.
Figure 22:
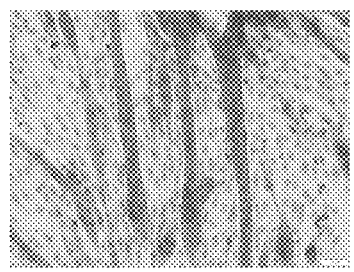
FIG. 22 shows the HE staining images of experimental group 20 in Example 18.
Figure 23:
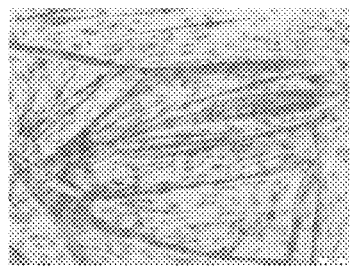
FIG. 23 shows the HE staining images of experimental group 21 in Example 18.
Figure 24:
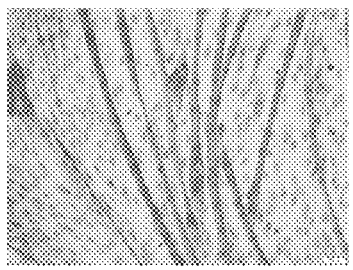
FIG. 24 shows the HE staining images of experimental group 22 in Example 18.
Figure 25:
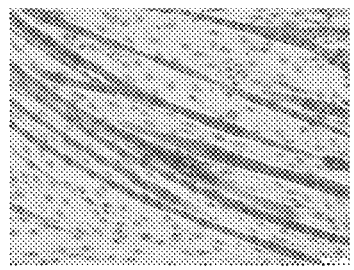
FIG. 25 shows the HE staining images of experimental group 23 in Example 18.
Figure 26:
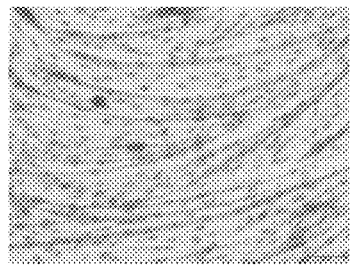
FIG. 26 shows the HE staining images of experimental group 24 in Example 18.
Figure 27:
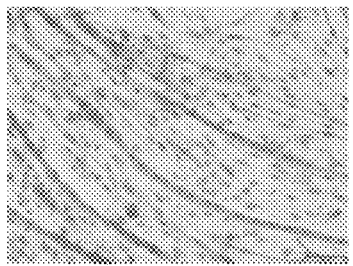
FIG. 27 shows the HE staining images of experimental group 25 in Example 18.
Figure 28:
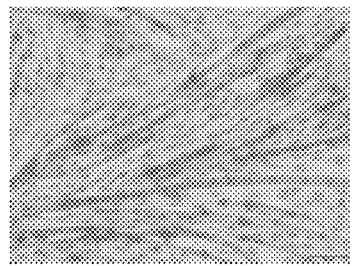
FIG. 28 shows the HE staining images of experimental group 26 in Example 18.
Figure 29:
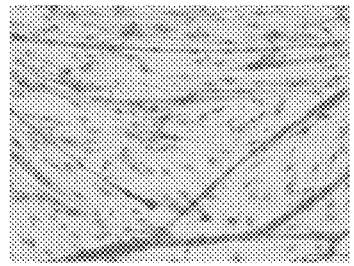
FIG. 29 shows the HE staining images of experimental group 27 in Example 18.
Figure 30:
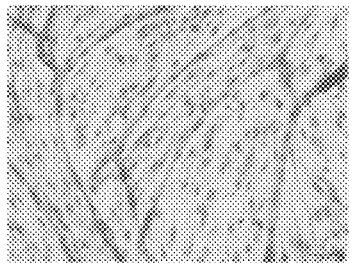
FIG. 30 shows the HE staining images of experimental group 28 in Example 18.
Figure 31:
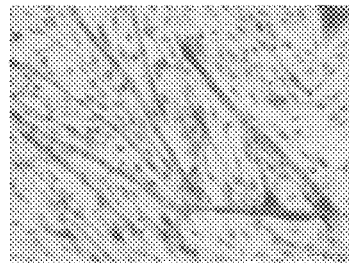
FIG. 31 shows the HE staining images of experimental group 29 in Example 18.
Figure 32:
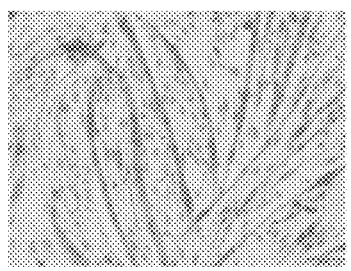
FIG. 32 shows the HE staining images of experimental group 30 in Example 18.
Figure 33:
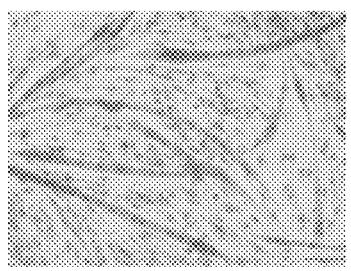
FIG. 33 shows the HE staining images of experimental group 31 in Example 18.
Figure 34:
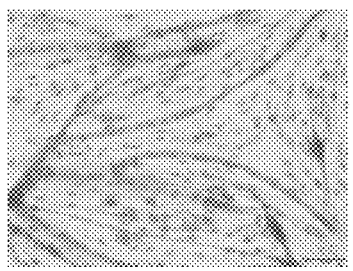
FIG. 34 shows the HE staining images of experimental group 32 in Example 18.
Figure 35:
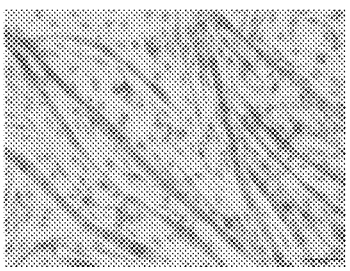
FIG. 35 shows the HE staining images of experimental group 33 in Example 18.
Figure 36:
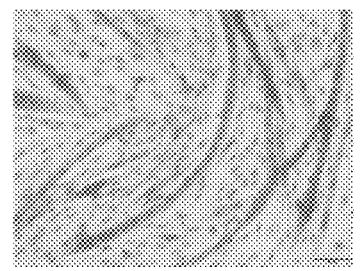
FIG. 36 shows the HE staining images of experimental group 34 in Example 18.
Figure 37:
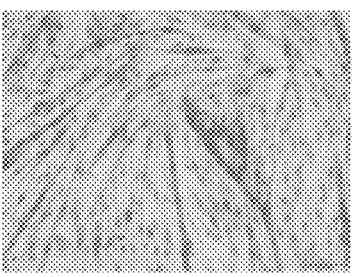
FIG. 37 shows the HE staining images of experimental group 35 in Example 18.
Figure 38:
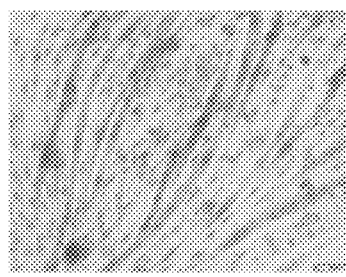
FIG. 38 shows the HE staining images of experimental group 36 in Example 18.
Figure 39:
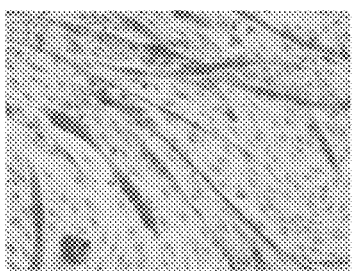
FIG. 39 shows the HE staining images of experimental group 37 in Example 18.
Figure 40:
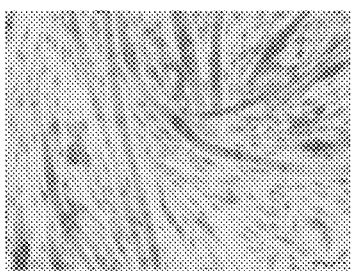
FIG. 40 shows the HE staining images of experimental group 38 in Example 18.
Figure 41:
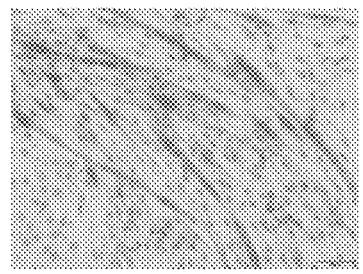
FIG. 41 shows the HE staining images of experimental group 39 in Example 18.
Figure 42:
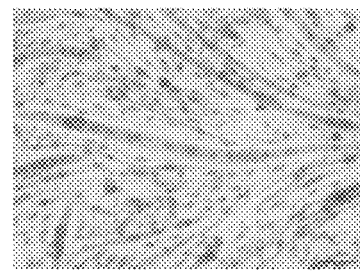
FIG. 42 shows the HE staining images of experimental group 40 in Example 18.
Figure 43:
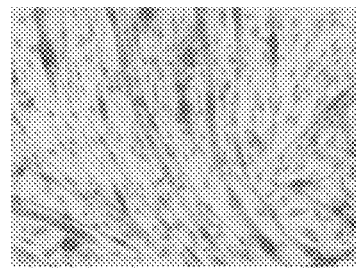
FIG. 43 shows the HE staining images of experimental group 41 in Example 18.
Figure 44:
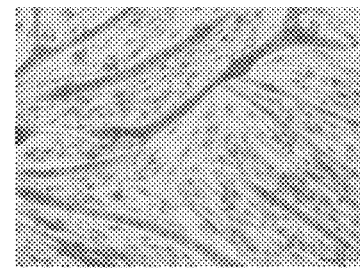
FIG. 44 shows the HE staining images of experimental group 42 in Example 18.
Figure 45:
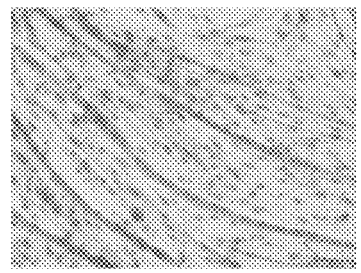
FIG. 45 shows the HE staining images of experimental group 43 in Example 18.
Figure 46:
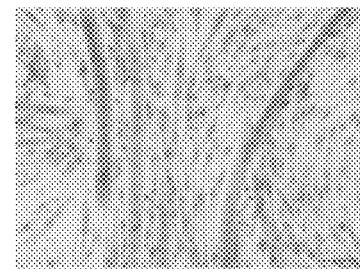
FIG. 46 shows the HE staining images of experimental group 44 in Example 18.

In order to improve the drawbacks and defects of existing technology, the present invention relates to a series of carbamo(dithioperoxo)thioate compound, its preparation and application in the treatment of cachexia, especially cancer cachexia and related diseases.

The present invention provides novel carbamo(dithioperoxo)thioate compounds with good anti-cachexia activity, especially carbamo(dithioperoxo)thioate compounds with nitrogen-containing aliphatic heterocyclic ring as shown in the formula (I):

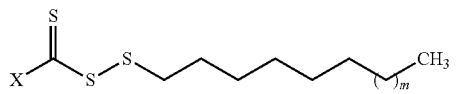

(I)

Wherein, m=1-11, preferably, m=1-9.

X is a nitrogen-containing aliphatic heterocyclic ring and the nitrogen atom in the aliphatic heterocyclic ring is connected to the carbon atom of the thiocarbonyl group.

Preferably, X is selected from four-membered nitrogen-containing aliphatic heterocyclic ring and its fused-ring heterocyclic derivatives or spirocyclic derivatives, five-membered nitrogen-containing aliphatic heterocyclic ring and its fused-ring heterocyclic derivatives or spirocyclic derivatives, six-membered nitrogen-containing aliphatic heterocyclic ring and its fused-ring heterocyclic derivatives or spirocyclic derivatives, Further preferably, X is selected from pyrrolidine, substituted pyrrolidine, piperidine, morpholine, azetidine, piperazine, indoline, isoindolin, octahydro-1H-indole, octahydro-1H-isoindole, 2-oxa-6-azaspiro[3.4]octane.

The present invention relates to following compounds 1, 2, 3, 4, 5, 6, 7, 8, 9, 10, 11, 12, 13, 14, 15, 16, 17:

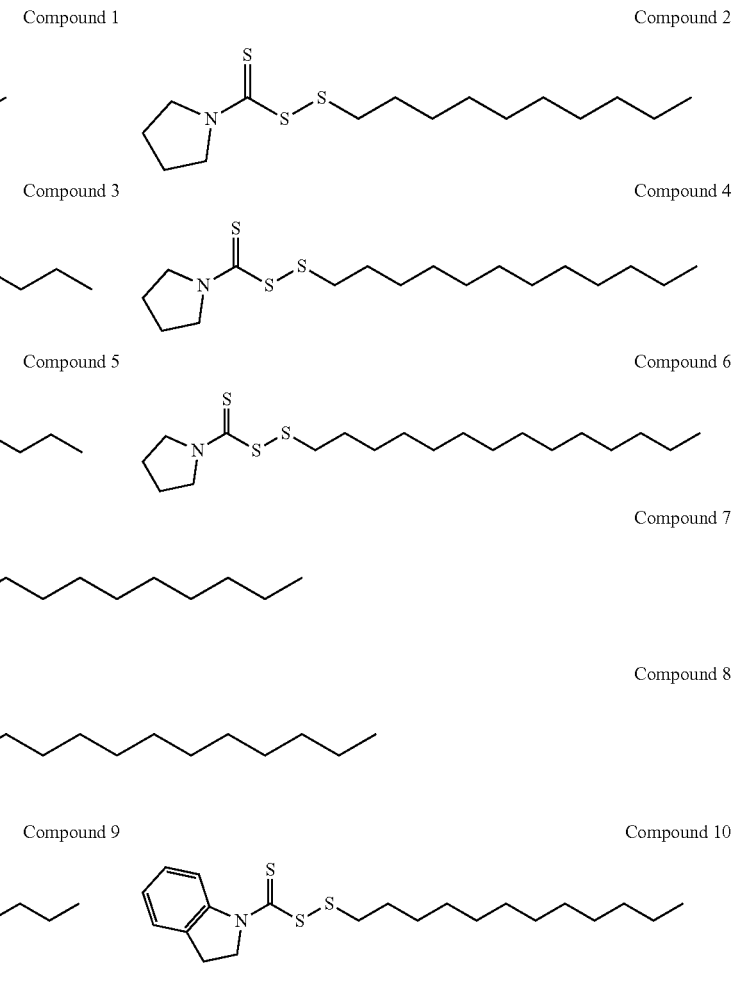

The present invention also relates to the application of carbamo(dithioperoxo)thioate compounds in the treatment of cachexia, especially cancer cachexia and related diseases.

The present invention also aims to provide the method to prepare carbamo(dithioperoxo)thioate compounds, especially the preparation of carbamo(dithioperoxo) thioate compounds with nitrogen-containing aliphatic heterocyclic ring.

Taking compound 1 for example, the method of preparing the compounds in the present invention is shown as following:

The method of pharmacology experiment adopted in the present invention is well known to technician in this research field.

In the present invention, the C2C12 cells (mouse myoblasts), 3T3-L1 cells (mouse adipocytes) and C26 cells (mouse colon cancer cells), used in the present invention, were obtained from the cell bank of the Type Culture Collection, Chinese Academy of Sciences. BALB/c mice were obtained from Shanghai Lingchang Biotechnology Co., Ltd.

In the present invention, petroleum ether (boiling point 60-90° C.), purchased from Sinopharm Chemical Reagent Co., Ltd.

FBS (fetal bovine serum), purchased from Biological Industries Co., Ltd.

Horse serum, purchased from Gibco Co., Ltd.

High glucose DMEM medium, purchased from Hyclone Co., Ltd.

RPMI-1640 medium, purchased from Hyclone Co., Ltd.

Phenol red-free high glucose DMEM medium, purchased from Hyclone Co., Ltd.

P/S antibiotics (penicillin-streptomycin) was purchased from Hyclone Co., Ltd.

Dexamethasone, purchased from Sigma-Aldrich Co., Ltd.

IBMX (3-isobutyl-1-methylxanthine) broad-spectrum phosphodiesterase inhibitor, purchased from Sigma-Aldrich Co., Ltd.

Human recombinant insulin was purchased from Shanghai Jinmai Bio. Co., Ltd.

Glycerol detection kit was purchased from Beijing Prilai Gene Technology Co., Ltd.

High glucose DMEM medium containing 10% FBS (the composition is 10% FBS+1% P/S+89% high glucose DMEM medium).

RPMI 1640 medium containing 10% FBS (the composition is: 10% FBS+1% P/S+89% RPMI-1640 medium). 2% HS differentiation medium (the composition is: 2% HS+1% P/S+97% high glucose DMEM medium).

The information of instruments used in the following examples are listed as:

Instruments used in chemical synthesis:

Rotary Evaporator: Buchi, Rotavapor R-200:

Column chromatography: Silica gel (200-300 mesh) and thin-layer chromatography plates were purchased from Sinopharm Chemical Reagent Co., Ltd.

Instruments used in the structure characterization and analysis:

Fluorescence microscope: Olympus, IX-73. $^1$H NMR, $^{13}$C NMR: Varian Model Mercury 400 MHz.

The preparation and application of carbamo(dithiperoxo)thioate compound in the present invention is further exemplified as following.

Example 1: Synthesis of Compound 1

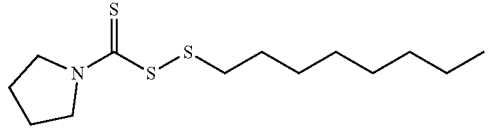

Pyrrolidine (58 µL, 0.70 mmol) and octane-1-thiol (122 µL, 0.70 mmol) were added in anhydrous dichloromethane (10 mL), the reaction mixture was cooled in an ice bath. Carbon disulfide (43 µL, 0.70 mmol) was then added dropwise, followed by slow addition of triethylamine (108 µL, 0.77 mmol). After a further five minutes, a solution of $CBr_4$ (466 mg, 1.41 mmol) in dichloromethane was added, followed by stirring at room temperature for two hours. The solution was washed with water (3×10 mL), saturated NaCl solution (2×10 mL) and dried over sodium sulfate. The product was further purified by column chromatography (DCM:PE=1:1) to yield the white solid (121 mg, 59.3%). $^1$H NMR (400 MHz, Chloroform-d): δ 3.97 (t, J=7.0 Hz, 2H), 3.75 (t, J=6.9 Hz, 2H), 2.86 (t, J=7.4 Hz, 2H), 2.12 (p, J=6.9 Hz, 2H), 2.00 (p, J=6.9 Hz, 2H), 1.67 (p, J=7.4 Hz, 2H), 1.39 (p, J=6.9 Hz, 2H), 1.27 (q, J=5.9, 5.3 Hz, 8H), 0.88 (t, J=6.6 Hz, 3H).

Example 2: Synthesis of Compound 2

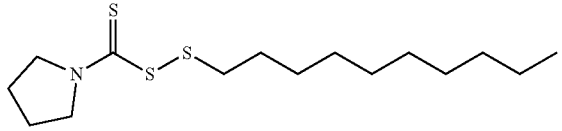

Pyrrolidine (58 µL, 0.70 mmol) and decane-1-thiol (146 µL, 0.70 mmol) were added in anhydrous dichloromethane (10 mL), the reaction mixture was cooled in an ice bath. Carbon disulfide (43 µL, 0.70 mmol) was then added dropwise, followed by slow addition of triethylamine (108 µL, 0.77 mmol). After a further five minutes, a solution of $CBr_4$ (466 mg, 1.41 mmol) in dichloromethane was added, followed by stirring at room temperature for two hours. The solution was washed with water (3×10 mL), saturated NaCl solution (2×10 mL) and dried over sodium sulfate. The product was further purified by column chromatography (DCM:PE=1:1) to yield the white solid (139 mg, 62.1%). $^1$H NMR (400 MHz, Chloroform-d): δ 3.97 (t, J=7.0 Hz, 2H), 3.75 (t, J=6.9 Hz, 2H), 2.86 (t, J=7.4 Hz, 2H), 2.12 (p, J=6.8 Hz, 2H), 2.00 (p, J=6.9 Hz, 2H), 1.68 (q, J=7.3 Hz, 2H), 1.39 (p, J=6.9 Hz, 2H), 1.27 (d, J=5.8 Hz, 12H), 0.88 (t, J=6.7 Hz, 3H). $^{13}$C NMR (150 MHz, Chloroform-d): δ 193.02, 56.64, 50.53, 38.69, 31.89, 29.54, 29.49, 29.31, 29.21, 28.63, 28.58, 26.51, 24.20, 22.68, 14.12.

Example 3: Synthesis of Compound 3

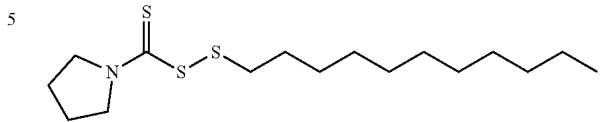

Pyrrolidine (83 mg, 1.17 mmol) and undecane-1-thiol (219 mg, 1.17 mmol) were added in anhydrous dichloromethane (10 mL), the reaction mixture was cooled in an ice bath. Carbon disulfide (71 µL, 1.17 mmol) was then added dropwise, followed by slow addition of triethylamine (178 µL, 1.29 mmol). After a further five minutes, a solution of $CBr_4$ (776 mg, 2.34 mmol) in dichloromethane was added, followed by stirring at room temperature for two hours. The solution was washed with water (3×10 mL), saturated NaCl solution (2×10 mL) and dried over sodium sulfate. The product was further purified by column chromatography (EA:PE=1:25) to yield the white solid (230 mg, 59%). $^1$H NMR (400 MHz, Chloroform-d) δ 3.68 (t, J=6.1 Hz, 2H), 3.39 (t, J=6.0 Hz, 2H), 3.03 (t, J=7.2 Hz, 2H), 1.90-1.77 (m, 2H), 1.77-1.65 (m, 2H), 1.51-1.37 (m, 2H), 1.16 (s, 2H), 1.00 (s, 14H), 0.62 (t, J=5.5 Hz, 3H). $^{13}$C NMR (151 MHz, Chloroform-d) δ 192.86, 54.20, 49.92, 35.98, 31.28, 28.97, 28.88, 28.70, 28.59, 28.36, 28.23, 25.40, 23.66, 22.05, 13.48.

Example 4: Synthesis of Compound 4

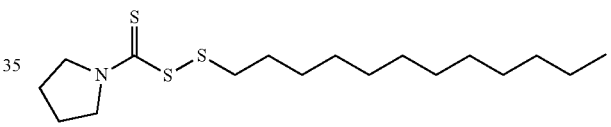

Pyrrolidine (58 µL, 0.70 mmol) and dodecane-1-thiol (168 µL, 0.70 mmol) were added in anhydrous dichloromethane (10 mL), the reaction mixture was cooled in an ice bath. Carbon disulfide (43 µL, 0.70 mmol) was then added dropwise, followed by slow addition of triethylamine (108 µL, 0.77 mmol). After a further five minutes, a solution of $CBr_4$ (466 mg, 1.41 mmol) in dichloromethane was added, followed by stirring at room temperature for two hours. The solution was washed with water (3×10 mL), saturated NaCl solution (2×10 mL) and dried over sodium sulfate. The product was further purified by column chromatography (DCM:PE=1:1) to yield the white solid (141 mg, 58%). $^1$H NMR (400 MHz, Chloroform-d): δ 3.97 (t, J=7.0 Hz, 2H), 3.75 (t, J=6.8 Hz, 2H), 2.86 (t, J=7.4 Hz, 2H), 2.12 (p, J=6.8 Hz, 2H), 2.00 (p, J=6.6 Hz, 2H), 1.66 (p, J=7.2 Hz, 2H), 1.38 (d, J=7.8 Hz, 2H), 1.25 (s, 16H), 0.88 (t, J=6.6 Hz, 3H). $^{13}$C NMR (150 MHz, Chloroform-d): δ 193.07, 56.63, 50.52, 38.73, 31.92, 29.64, 29.59, 29.50, 29.35, 29.22, 28.65, 28.59, 26.51, 24.20, 22.69, 14.12.

Example 5: Synthesis of Compound 5

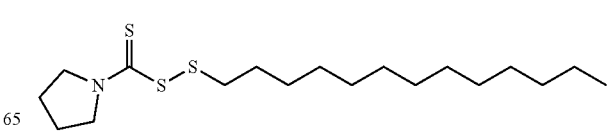

Pyrrolidine (83 mg, 1.17 mmol) and tridecane-1-thiol (250 mg, 1.16 mmol) were added in anhydrous dichloromethane (10 mL), the reaction mixture was cooled in an ice bath. Carbon disulfide (71 μL, 1.17 mmol) was then added dropwise, followed by slow addition of triethylamine (178 μL, 1.29 mmol). After a further five minutes, a solution of CBr$_4$ (776 mg, 2.34 mmol) in dichloromethane was added, followed by stirring at room temperature for two hours. The solution was washed with water (3×10 mL), saturated NaCl solution (2×10 mL) and dried over sodium sulfate. The product was further purified by column chromatography (EA:PE=1:25) to yield the white solid (100 mg, 27%). $^1$H NMR (400 MHz, Chloroform-d) δ 3.91 (t, J=6.8 Hz, 2H), 3.62 (t, J=6.8 Hz, 2H), 3.26 (t, J=7.4 Hz, 2H), 2.11-2.00 (m, 2H), 1.96 (dd, J=13.5, 6.7 Hz, 2H), 1.66 (dd, J=14.7, 7.2 Hz, 2H), 1.40 (dd, J=14.8, 8.5 Hz, 2H), 1.24 (s, 18H), 0.85 (t, J=6.3 Hz, 3H). $^{13}$C NMR (151 MHz, Chloroform-d) δ 192.71, 54.35, 49.92, 36.15, 31.29, 29.04, 29.02, 28.97, 28.88, 28.72, 28.59, 28.37, 28.23, 25.40, 23.67, 22.06, 13.48.

Example 6: Synthesis of Compound 6

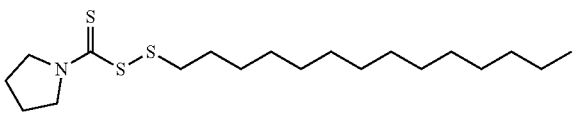

Pyrrolidine (58 μL, 0.70 mmol) and tetradecane-1-thiol (191 μL, 0.70 mmol) were added in anhydrous dichloromethane (10 mL), the reaction mixture was cooled in an ice bath. Carbon disulfide (43 μL, 0.70 mmol) was then added dropwise, followed by slow addition of triethylamine (108 μL, 0.77 mmol). After a further five minutes, a solution of CBr$_4$ (466 mg, 1.41 mmol) in dichloromethane was added, followed by stirring at room temperature for two hours. The solution was washed with water (3×10 mL), saturated NaCl solution (2×10 mL) and dried over sodium sulfate. The product was further purified by column chromatography (EA:PE=1:1) to yield the white solid (140 mg, 53.1%). $^1$H NMR (400 MHz, Chloroform-d): δ 3.97 (t, J=7.0 Hz, 2H), 3.75 (t, J=6.9 Hz, 2H), 2.86 (t, J=7.4 Hz, 2H), 2.12 (p, J=6.9 Hz, 2H), 2.00 (p, J=6.9 Hz, 2H), 1.68 (q, J=7.4 Hz, 2H), 1.46-1.34 (m, 2H), 1.26 (s, 20H), 0.93-0.83 (m, 3H). $^{13}$C NMR (150 MHz, Chloroform-d): δ 192.99, 56.63, 50.53, 38.69, 31.93, 29.69, 29.65, 29.58, 29.49, 29.36, 29.21, 28.64, 28.57, 26.51, 24.20, 22.69, 14.13.

Example 7: Synthesis of Compound 7

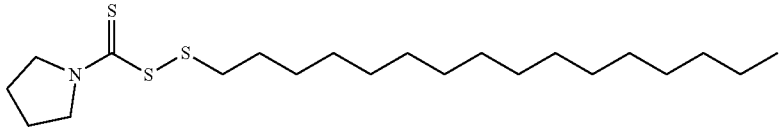 [SMILES: CCCCCCCCCCCCCCCCSSC(=S)N1CCCC1]

Pyrrolidine (58 μL, 0.70 mmol) and hexadecane-1-thiol (216 μL, 0.70 mmol) were added in anhydrous dichloromethane (10 mL), the reaction mixture was cooled in an ice bath. Carbon disulfide (43 μL, 0.70 mmol) was then added dropwise, followed by slow addition of triethylamine (108 μL, 0.77 mmol). After a further five minutes, a solution of CBr$_4$ (466 mg, 1.41 mmol) in dichloromethane was added, followed by stirring at room temperature for two hours. The solution was washed with water (3×10 mL), saturated NaCl solution (2×10 mL) and dried over sodium sulfate. The product was further purified by column chromatography (DCM:PE=1:1) to yield the white solid (161 mg, 56.8%). $^1$H NMR (400 MHz, Chloroform-d): δ 3.97 (t, J=7.0 Hz, 2H), 3.75 (t, J=6.9 Hz, 2H), 2.86 (t, J=7.4 Hz, 2H), 2.12 (p, J=6.9 Hz, 2H), 2.00 (p, J=6.9 Hz, 2H), 1.66 (p, J=7.5 Hz, 2H), 1.40 (d, J=7.4 Hz, 2H), 1.25 (s, 26H), 0.88 (t, J=6.5 Hz, 3H). $^{13}$C NMR (150 MHz, Chloroform-d): δ 193.06, 56.63, 50.52, 38.73, 31.94, 29.70, 29.66, 29.59, 29.50, 29.37, 29.22, 28.65, 28.59, 26.51, 24.20, 22.70, 14.12.

Example 8: Synthesis of Compound 8

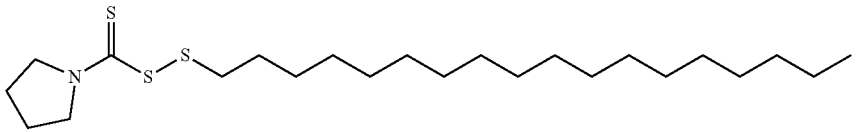 [SMILES: CCCCCCCCCCCCCCCCCCSSC(=S)N1CCCC1]

Pyrrolidine (58 μL, 0.70 mmol) and octadecane-1-thiol (238 μL, 0.70 mmol) were added in anhydrous dichloromethane (10 mL), the reaction mixture was cooled in an ice bath. Carbon disulfide (43 μL, 0.70 mmol) was then added dropwise, followed by slow addition of triethylamine (108 μL, 0.77 mmol). After a further five minutes, a solution of CBr$_4$ (466 mg, 1.41 mmol) in dichloromethane was added, followed by stirring at room temperature for two hours. The solution was washed with water (3×10 mL), saturated NaCl solution (2×10 mL) and dried over sodium sulfate. The product was further purified by column chromatography (DCM:PE=1:1) to yield the white solid (154 mg, 50.9%). $^1$H NMR (400 MHz, Chloroform-d): δ 3.97 (t, J=7.0 Hz, 2H), 3.75 (t, J=6.9 Hz, 2H), 2.86 (t, J=7.4 Hz, 2H), 2.12 (p, J=6.8 Hz, 2H), 2.00 (p, J=6.9 Hz, 2H), 1.66 (p, J=7.4 Hz, 2H), 1.38 (q, J=7.1 Hz, 2H), 1.25 (s, 28H), 0.88 (t, J=6.6 Hz, 3H). $^{13}$C NMR (150 MHz, Chloroform-d): δ 193.06, 56.63, 50.52, 38.73, 31.94, 29.71, 29.67, 29.59, 29.50, 29.37, 29.33, 29.22, 28.65, 28.59, 26.51, 24.20, 22.70, 14.12.

Example 9: Synthesis of Compound 9

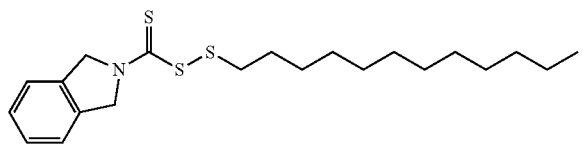 [SMILES: CCCCCCCCCCCCSSC(=S)N1Cc2ccccc2C1]

Isoindoline (132 µL, 1.17 mmol) and dodecane-1-thiol (237 mg, 1.17 mmol) were added in anhydrous dichloromethane (10 mL), the reaction mixture was cooled in an ice bath. Carbon disulfide (71 µL, 1.17 mmol) was then added dropwise, followed by slow addition of triethylamine (178 µL, 1.29 mmol). After a further five minutes, a solution of $CBr_4$ (776 mg, 2.34 mmol) in dichloromethane was added, followed by stirring at room temperature for two hours. The solution was washed with water (3×10 mL), saturated NaCl solution (2×10 mL) and dried over sodium sulfate. The product was further purified by column chromatography (EA:PE=1:25) to yield the white solid (270 mg, 58%). $^1$H NMR (400 MHz, Chloroform-d) δ 7.38-7.26 (m, 4H), 5.24 (s, 2H), 5.07 (s, 2H), 2.89 (t, J=7.1 Hz, 2H), 1.79-1.63 (m, 2H), 1.40 (s, 2H), 1.25 (s, 16H), 0.88 (t, J=6.2 Hz, 3H). $^{13}$C NMR (151 MHz, Chloroform-d) δ 193.52, 134.19, 127.38, 122.11, 61.32, 54.98, 38.05, 31.29, 29.02, 29.01, 28.96, 28.87, 28.72, 28.58, 28.05, 27.95, 22.07, 13.50.

Example 10: Synthesis of Compound 10

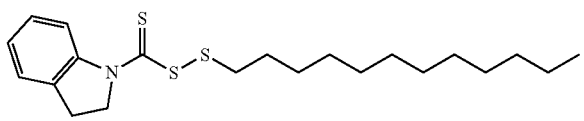 [SMILES: CCCCCCCCCCCCSSC(=S)N1CCc2ccccc21]

Indoline (130 µL, 1.17 mmol) and dodecane-1-thiol (237 mg, 1.17 mmol) were added in anhydrous dichloromethane (10 mL), the reaction mixture was cooled in an ice bath. Carbon disulfide (71 µL, 1.17 mmol) was then added dropwise, followed by slow addition of triethylamine (178 µL, 1.29 mmol). After a further five minutes, a solution of $CBr_4$ (776 mg, 2.34 mmol) in dichloromethane was added, followed by stirring at room temperature for two hours. The solution was washed with water (3×20 mL), saturated NaCl solution (10 mL) and dried over sodium sulfate. The product was further purified by column chromatography (EA:PE=1:25) to yield the yellow oil (125 mg, 27%). $^1$H NMR (400 MHz, Chloroform-d) δ 7.12 (t, J=7.4 Hz, 1H), 7.06 (d, J=6.7 Hz, 1H), 6.91 (d, J=7.6 Hz, 1H), 6.73 (t, J=7.0 Hz, 1H), 3.70 (t, J=8.4 Hz, 2H), 3.01 (t, J=8.2 Hz, 2H), 2.69 (t, J=7.3 Hz, 2H), 1.62-1.54 (m, 2H), 1.38 (s, 2H), 1.25 (s, 16H), 0.88 (s, 3H). $^{13}$C NMR (151 MHz, Chloroform-d) δ 151.76, 128.69, 126.84, 123.85, 118.35, 108.67, 56.19, 34.68, 31.32, 29.04, 28.99, 28.92, 28.75, 28.69, 28.33, 28.19, 27.78, 22.09, 13.53.

Example 11: Synthesis of Compound 11

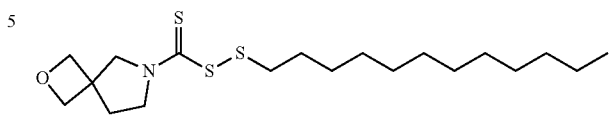

2-Oxa-6-azaspiro[3.4]octane (132 mg, 1.17 mmol) and dodecane-1-thiol (237 mg, 1.17 mmol) were added in anhydrous dichloromethane (10 mL), the reaction mixture was cooled in an ice bath. Carbon disulfide (71 µL, 1.17 mmol) was then added dropwise, followed by slow addition of triethylamine (178 µL, 1.29 mmol). After a further five minutes, a solution of $CBr_4$ (776 mg, 2.34 mmol) in dichloromethane was added, followed by stirring at room temperature for two hours. The solution was washed with water (3×20 mL), saturated NaCl solution (10 mL) and dried over sodium sulfate. The product was further purified by column chromatography (EA:PE=1:3) to yield the white solid (180 mg, 40%). $^1$H NMR (400 MHz, Chloroform-d) δ 4.43 (ddd, J=19.4, 17.9, 6.1 Hz, 4H), 3.96 (s, 1H), 3.75 (s, 2H), 3.55 (t, J=6.7 Hz, 1H), 2.61 (t, J=6.9 Hz, 2H), 2.19 (t, J=6.8 Hz, 1H), 2.06 (t, J=7.0 Hz, 1H), 1.42 (s, 2H), 1.15 (s, 2H), 1.01 (s, 16H), 0.64 (t, J=6.3 Hz, 3H). $^{13}$C NMR (151 MHz, Chloroform-d) δ 193.52, 79.55, 63.48, 57.81, 54.22, 48.50, 45.78, 43.13, 38.04, 35.42, 33.17, 31.17, 29.00, 28.94, 28.85, 28.71, 28.57, 28.03, 27.92, 22.05, 13.49.

Example 12: Synthesis of Compound 12

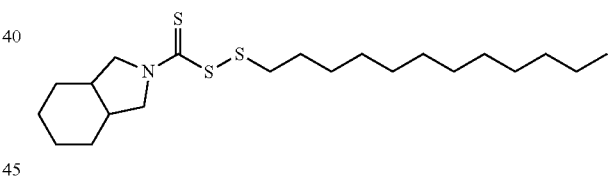

Octahydro-1H-isoindole (147 mg, 1.17 mmol) and dodecane-1-thiol (237 mg, 1.17 mmol) were added in anhydrous dichloromethane (10 mL), the reaction mixture was cooled in an ice bath. Carbon disulfide (71 µL, 1.17 mmol) was then added dropwise, followed by slow addition of triethylamine (178 µL, 1.29 mmol). After a further five minutes, a solution of $CBr_4$ (776 mg, 2.34 mmol) in dichloromethane was added, followed by stirring at room temperature for two hours. The solution was washed with water (3×20 mL), saturated NaCl solution (10 mL) and dried over sodium sulfate. The product was further purified by column chromatography (EA:PE=1:25) to yield the yellow oil (360 mg, 76%). $^1$H NMR (400 MHz, Chloroform-d) δ 3.66 (dd, J=12.9, 7.4 Hz, 1H), 3.56 (dd, J=13.2, 6.3 Hz, 1H), 3.50-3.39 (m, 1H), 3.32 (dd, J=11.1, 5.7 Hz, 1H), 2.56 (t, J=7.3 Hz, 2H), 2.08 (ddd, J=33.1, 11.8, 5.9 Hz, 2H), 1.36 (dd, J=14.4, 7.5 Hz, 4H), 1.27-1.06 (m, 8H), 0.95 (s, 16H), 0.58 (t, J=6.4 Hz, 3H). $^{13}$C NMR (151 MHz, Chloroform-d) δ 193.54, 59.76, 53.96, 38.06, 37.53, 35.14, 31.30, 29.03, 29.01, 28.96, 28.88, 28.73, 28.59, 28.03, 27.95, 25.07, 24.92, 22.07, 21.98, 21.70, 13.51.

Example 13: Synthesis of Compound 13

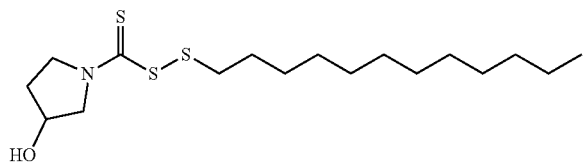 [SMILES: CCCCCCCCCCCCSSC(=S)N1CCC(O)C1]

3-Hydroxy pyrrolidine (174 mg, 2 mmol) and dodecane-1-thiol (404 mg, 2 mmol) were added in anhydrous dichloromethane (10 mL), the reaction mixture was cooled in an ice bath. Carbon disulfide (152 mg, 2 mmol) was then added dropwise, followed by slow addition of triethylamine (204 mg, 2.2 mmol). After a further five minutes, a solution of $CBr_4$ (1326 mg, 4 mmol) in dichloromethane was added, followed by stirring at room temperature for two hours. The solution was washed with water (3×10 mL), saturated NaCl solution (2×10 mL) and dried over sodium sulfate. The product was further purified by column chromatography (DCM:PE=1:6) to yield the white solid (150 mg, 22%). $^1$H NMR (400 MHz, Chloroform-d) δ 4.60 (s, 1H), 4.25-3.77 (overlap, 4H), 2.85 (t, J=7.1 Hz, 2H), 2.30-1.79 (overlap, 3H), 1.72-1.61 (m, 2H), 1.44-1.35 (m, 2H), 1.25 (s, 16H), 0.88 (t, J=6.3 Hz, 3H). $^{13}$C NMR (151 MHz, Chloroform-d) δ 194.12, 71.41, 68.99, 64.58, 54.18, 48.39, 38.73, 31.92, 29.64, 29.59, 29.50, 29.35, 29.22, 28.67, 28.58, 22.69, 14.12.

Example 14: Synthesis of Compound 14

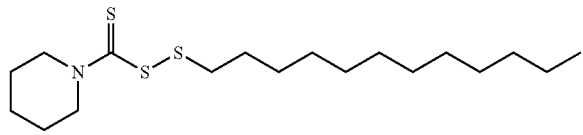 [SMILES: CCCCCCCCCCCCSSC(=S)N1CCCCC1]

Piperidine (100 mg, 1.17 mmol) and dodecane-1-thiol (237 mg, 1.17 mmol) were added in anhydrous dichloromethane (10 mL), the reaction mixture was cooled in an ice bath. Carbon disulfide (71 µL, 1.17 mmol) was then added dropwise, followed by slow addition of triethylamine (178 µL, 1.29 mmol). After a further five minutes, a solution of $CBr_4$ (776 mg, 2.34 mmol) in dichloromethane was added, followed by stirring at room temperature for two hours. The solution was washed with water (3×20 mL), saturated NaCl solution (10 mL) and dried over sodium sulfate. The product was further purified by column chromatography (EA:PE=1:25) to yield the white solid (210 mg, 50%). $^1$H NMR (400 MHz, Chloroform-d) δ 4.33 (s, 2H), 3.99 (s, 2H), 2.86 (t, J=6.1 Hz, 2H), 1.89-1.58 (m, 8H), 1.40 (s, 2H), 1.27 (s, 16H), 0.89 (s, 3H). $^{13}$C NMR (151 MHz, Chloroform-d) δ 195.98, 54.55, 51.21, 38.16, 31.27, 29.00, 28.98, 28.94, 28.85, 28.70, 28.56, 27.94, 25.62, 24.86, 23.55, 22.04, 13.48.

Example 15: Synthesis of Compound 15

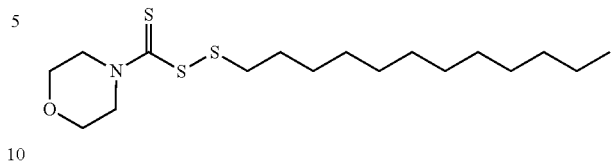

Morpholine (100 mg, 1.17 mmol) and dodecane-1-thiol (237 mg, 1.17 mmol) were added in anhydrous dichloromethane (10 mL), the reaction mixture was cooled in an ice bath. Carbon disulfide (71 µL, 1.17 mmol) was then added dropwise, followed by slow addition of triethylamine (178 µL, 1.29 mmol). After a further five minutes, a solution of $CBr_4$ (776 mg, 2.34 mmol) in dichloromethane was added, followed by stirring at room temperature for two hours. The solution was washed with water (3×20 mL), saturated NaCl solution (10 mL) and dried over sodium sulfate. The product was further purified by column chromatography (EA:PE=1:25) to yield the white solid (210 mg, 50%). $^1$H NMR (400 MHz, Chloroform-d) δ 4.36 (s, 2H), 4.07 (s, 2H), 3.79 (s, 4H), 2.86 (t, J=7.2 Hz, 2H), 1.73-1.58 (m, 2H), 1.40 (s, 2H), 1.26 (s, 16H), 0.89 (t, J=6.4 Hz, 3H). $^{13}$C NMR (151 MHz, Chloroform-d) δ 197.65, 65.65, 52.62, 50.54, 38.11, 31.27, 29.00, 28.98, 28.93, 28.84, 28.70, 28.55, 27.99, 27.92, 22.04, 13.49.

Example 16: Synthesis of Compound 16

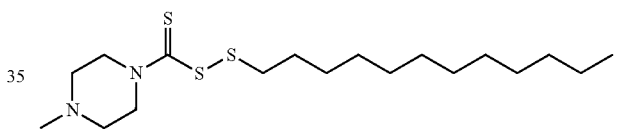

4-Methylpiperazine (180 mg, 1.8 mmol) and dodecane-1-thiol (363 mg, 1.8 mmol) were added in anhydrous dichloromethane (10 mL), the reaction mixture was cooled in an ice bath. Carbon disulfide (139 mg, 1.8 mmol) was then added dropwise, followed by slow addition of triethylamine (200 mg, 1.98 mmol). After a further five minutes, a solution of $CBr_4$ (1200 mg, 3.6 mmol) in dichloromethane was added, followed by stirring at room temperature for two hours. The solution was washed with water (3×10 mL), saturated NaCl solution (2×10 mL) and dried over sodium sulfate. The product was further purified by column chromatography (DCM:PE=1:3) to yield the white solid (270 mg, 40%). $^1$H NMR (400 MHz, Chloroform-d) δ 4.21 (brs, 4H), 2.85 (t, J=7.2 Hz, 2H), 2.53 (s, 4H), 2.34 (s, 3H), 1.76-1.55 (m, 2H), 1.39 (s, 2H), 1.25 (s, 16H), 0.87 (d, J=6.8 Hz, 3H). $^{13}$C NMR (151 MHz, Chloroform-d) δ 197.65, 54.45, 45.62, 38.75, 31.92, 29.65, 29.63, 29.58, 29.49, 29.35, 29.21, 28.60, 28.57, 22.69, 14.13.

Example 17: Synthesis of Compound 17

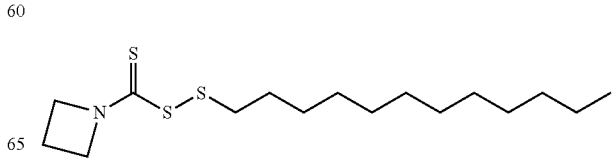

Azetidine hydrochloride (187 mg, 2 mmol) and potassium hydroxide (112 mg, 2 mmol) were mixed in THF (10 mL) and stirred for 2 h. The obtained azetidine and dodecane-1-thiol (0.48 mL, 2 mmol) were added in anhydrous dichloromethane (10 mL), the reaction mixture was cooled in an ice bath. Carbon disulfide (0.12 mL, 2 mmol) was then added dropwise, followed by slow addition of triethylamine (0.31 mL, 2.2 mmol). After a further five minutes, a solution of $CBr_4$ (1300 mg, 4 mmol) in dichloromethane was added, followed by stirring at room temperature for two hours. The solution was washed with water (3×10 mL), saturated NaCl solution (2×10 mL) and dried over sodium sulfate. The product was further purified by column chromatography (DCM:PE=1:8) to yield the pale-yellow solid (270 mg, 40%). $^1$H NMR (400 MHz, Chloroform-d) δ 4.35 (t, J=7.6 Hz, 4H), 2.83 (t, J=7.5 Hz, 2H), 2.49-2.39 (m, 2H), 1.72-1.62 (m, 2H), 1.38 (brs, 2H), 1.25 (s, 16H), 0.88 (s, 3H). $^{13}$C NMR (151 MHz, Chloroform-d) δ 193.88, 56.11, 53.94, 39.10, 31.92, 29.65, 29.58, 29.50, 29.35, 29.20, 28.68, 28.54, 22.69, 15.77, 14.12.

Example 18

Carbamo(dithioperoxo)thioate analogs alleviate mouse myoblasts (C2C12) atrophy induced by mouse colon cancer cell (C26).

The diameter measurement method was used to evaluate the diameter of myotubes differentiated from mouse myoblasts (C2C12). The staining method used in the experiment was hematoxylin-eosin staining, referred to as HE staining. The hematoxylin stain is alkaline, positively charged, and easily binds to negatively charged and acidic deoxyribonucleic acid (DNA) in the nucleus with ionic bonding to show blue; while eosin is an acidic dye that dissociates into negatively charged anions in water and easily binds to the positively charged amino groups of proteins in the cytoplasm to show red. The stained cells were placed under a high-magnification microscope to take photos (magnification power: 400), and the diameter of myotubes could be counted using image J software.

The above method allows to evaluate the effect of the drug on the muscle atrophy cell model. The specific method is as follows.

C2C12 cells were seeded in 24-well plates in a culture medium of high-glucose DMEM medium containing 10% FBS and 1% P/S, and placed in a 5% $CO_2$, 37° C. environment. When the cell density reaches 50%~60%, the culture medium was changed into 2% HS differentiation medium (high-glucose DMEM medium containing 2% HS and 1% P/S); the differentiation medium was changed every 48 h until mature on day 5 or day 6. In addition, C26 cells were inoculated in T75 flasks, and the culture medium was changed into high-glucose DMEM medium containing 10% FBS and 1% P/S, and placed in a 5% $CO_2$, 37° C. environment. While C26 cells ($6\times10^6$ cells/flasks) were passaged, add 20 mL of culture medium to sequentially subculture for 48 h. To obtain the C26 supernatant, centrifuge C26 culture medium at 1000 rpm for 3 min and then at 4000 rpm for 10 min successively. The C26 supermatant and 2% HS differentiation medium were mixed 1:1 (volume ratio) as a muscle atrophy inducing medium. Except for the control group with 2% HS differentiation medium, other each group was added with the equal amounts of muscle atrophy-inducing medium and one group was used as the model group, and the rest groups were used as the experimental groups for drug administration. At the same time, carbamo(dithioperoxo) thioate compounds were added into the cells at the following gradient concentrations.

TABLE 1

Administration samples for myotubes (C2C12) atrophy assay in example

| Ser. No. | No. | Test sample | Component |
|---|---|---|---|
| 1 | CT | Control group | 2% HS differentiation medium |
| 2 | C26 medium | Model group | 2% HS differentiation medium + C26 medium |
| 3 | C26 + 1(25 μM) | Experimental group 1 | 2% HS differentiation medium + C26 medium + 25 μM compound 1 |
| 4 | C26 + 1(50 μM) | Experimental group 2 | 2% HS differentiation medium + C26 medium + 50 μM compound 2 |
| 5 | C26 + 1(100 μM) | Experimental group 3 | 2% HS differentiation medium + C26 medium + 100 μM compound 3 |
| 6 | C26 + 2(12.5 μM) | Experimental group 4 | 2% HS differentiation medium + C26 medium + 12.5 μM compound 4 |
| 7 | C26 + 2(25 μM) | Experimental group 5 | 2% HS differentiation medium + C26 medium + 25 μM compound 5 |
| 8 | C26 + 2(50 μM) | Experimental group 6 | 2% HS differentiation medium + C26 medium + 50 μM compound 6 |
| 9 | C26 + 3(25 μM) | Experimental group 7 | 2% HS differentiation medium + C26 medium + 25 μM compound 7 |
| 10 | C26 + 3(50 μM) | Experimental group 8 | 2% HS differentiation medium + C26 medium + 50 μM compound 8 |
| 11 | C26 + 3(100 μM) | Experimental group 9 | 2% HS differentiation medium + C26 medium + 100 μM compound 9 |
| 12 | C26 + 4(3.125 μM) | Experimental group 10 | 2% HS differentiation medium + C26 medium + 3.125 μM compound 10 |
| 13 | C26 + 4(6.25 μM) | Experimental group 11 | 2% HS differentiation medium + C26 medium + 6.25 μM compound 11 |
| 14 | C26 + 4(12.5 μM) | Experimental group 12 | 2% HS differentiation medium + C26 medium + 12.5 μM compound 12 |
| 15 | C26 + 5(25 μM) | Experimental group 13 | 2% HS differentiation medium + C26 medium + 25 μM compound 13 |
| 16 | C26 + 5(50 μM) | Experimental group 14 | 2% HS differentiation medium + C26 medium + 50 μM compound 14 |
| 17 | C26 + 6(25 μM) | Experimental group 15 | 2% HS differentiation medium + C26 medium + 25 μM compound 15 |

TABLE 1-continued

Administration samples for myotubes (C2C12) atrophy assay in example

| Ser. No. | No. | Test sample | Component |
|---|---|---|---|
| 18 | C26 + 6(50μM) | Experimental group 16 | 2% HS differentiation medium + C26 medium + 50 μM compound 16 |
| 19 | C26 + 6(100 μM) | Experimental group 17 | 2% HS differentiation medium + C26 medium + 100 μM compound 17 |
| 20 | C26 + 7(25 μM) | Experimental group 18 | 2% HS differentiation medium + C26 medium + 25 μM compound 18 |
| 21 | C26 + 7(50 μM) | Experimental group 19 | 2% HS differentiation medium + C26 medium + 50 μM compound 19 |
| 22 | C26 + 7(100 μM) | Experimental group 20 | 2% HS differentiation medium + C26 medium + 100 μM compound 20 |
| 23 | C26 + 8(25 μM) | Experimental group 21 | 2% HS differentiation medium + C26 medium + 25 μM compound 21 |
| 24 | C26 + 8(50 μM) | Experimental group 22 | 2% HS differentiation medium + C26 medium + 50 μM compound 22 |
| 25 | C26 + 8(100 μM) | Experimental group 23 | 2% HS differentiation medium + C26 medium + 100 μM compound 23 |
| 26 | C26 + 9(25 μM) | Experimental group 24 | 2% HS differentiation medium + C26 medium + 25 μM compound 24 |
| 27 | C26 + 9(50 μM) | Experimental group 25 | 2% HS differentiation medium + C26 medium + 50 μM compound 25 |
| 28 | C26 + 9(100 μM) | Experimental group 26 | 2% HS differentiation medium + C26 medium + 100 μM compound 26 |
| 29 | C26 + 10(25 μM) | Experimental group 27 | 2% HS differentiation medium + C26 medium + 25 μM compound 27 |
| 30 | C26 + 10(50 μM) | Experimental group 28 | 2% HS differentiation medium + C26 medium + 50 μM compound 28 |
| 31 | C26 + 10(100 μM) | Experimental group 29 | 2% HS differentiation medium + C26 medium + 100 μM compound 29 |
| 32 | C26 + 11(25 μM) | Experimental group 30 | 2% HS differentiation medium + C26 medium + 25 μM compound 30 |
| 33 | C26 + 11(50 μM) | Experimental group 31 | 2% HS differentiation medium + C26 medium + 50 μM compound 31 |
| 34 | C26 + 12(25 μM) | Experimental group 32 | 2% HS differentiation medium + C26 medium + 25 μM compound 32 |
| 35 | C26 + 12(50 μM) | Experimental group 33 | 2% HS differentiation medium + C26 medium + 50 μM compound 33 |
| 36 | C26 + 12(100 μM) | Experimental group 34 | 2% HS differentiation medium + C26 medium + 100 μM compound 34 |
| 37 | C26 + 13(25 μM) | Experimental group 35 | 2% HS differentiation medium + C26 medium + 25 μM compound 35 |
| 38 | C26 + 13(50 μM) | Experimental group 36 | 2% HS differentiation medium + C26 medium + 50 μM compound 36 |
| 39 | C26 + 14(25 μM) | Experimental group 37 | 2% HS differentiation medium + C26 medium + 25 μM compound 37 |
| 40 | C26 + 14(50 μM) | Experimental group 38 | 2% HS differentiation medium + C26 medium + 50 μM compound 38 |
| 41 | C26 + 15(25 μM) | Experimental group 39 | 2% HS differentiation medium + C26 medium + 25 μM compound 39 |
| 42 | C26 + 15(50 μM) | Experimental group 40 | 2% HS differentiation medium + C26 medium + 50 μM compound 40 |
| 43 | C26 + 16(25 μM) | Experimental group 41 | 2% HS differentiation medium + C26 medium + 25 μM compound 41 |
| 44 | C26 + 16(50 μM) | Experimental group 42 | 2% HS differentiation medium + C26 medium + 50 μM compound 42 |
| 45 | C26 + 17(25 μM) | Experimental group 43 | 2% HS differentiation medium + C26 medium + 25 μM compound 43 |
| 46 | C26 + 17(50 μM) | Experimental group 44 | 2% HS differentiation medium + C26 medium + 50 μM compound 44 |

Wherein, the serial numbers correspond to the numbers of the accompanying figures, that is, FIG. 1-46 correspond to the samples of serial numbers 1-46 in Table 1. μM refers to μmol/L.

Myotube diameter was measured as follows.

After 48 h of action, the myotubes were fixed with fixative solution (anhydrous ethanol:formaldehyde:glacial acetic acid volume ratio=20:2:1) for more than 1 h, stained using hematoxylin-eosin staining method, and placed under a high-magnification microscope to acquire images and counted the diameter of myotubes using image J. The muscle atrophy reversal rate was calculated according to the following equation.

Muscle atrophy reversal rate=(Average value of myotubes in drug administration group−Average value of myotubes in model group)/(Average value of myotubes in control group−Average value of myotubes in model group)×100%

Results and Conclusions

Appendix FIGS. 1-46 are representative images of HE staining of carbamo(dithioperoxo) thioate analogues alleviating C2C12 mature myotubes atrophy induced by C26 cell culture medium, and the appendix Table 2 is a table of myotube statistical results. As shown in FIGS. 1-46 and Table 2, carbamo(dithioperoxo)thioate analogs showed a significant reversal of myotube atrophy in a concentration-dependent manner. From the results, it can be found that the long-chain substituted carbamo(dithioperoxo)thioate basically have better reversal of myotube atrophy, but their activities are closely correlated with the chain length. Among them, compound 4 has the most significant effect with 92.83% reversal of myotube atrophy at a non-cytotoxic 12.5 μM. This compound serves as a candidate for further research and development. However, the activity was lower when the chain length was 18 carbon atoms (compound 8).

TABLE 2

Statistical results table of myotubes

| Compound No. | Myotube atrophy reversal rate (%) | | |
|---|---|---|---|
| | 25 μM | 50 μM | 100 μM |
| Compound 1 | 18.39% | 2.51% | 36.26% |
| Compound 2 | 16.94% (12.5 μM) | 43.90% (25 μM) | 61.05% (50 μM) |
| Compound 3 | 35.76% | 33.40% | 46.11% |
| Compound 4 | 37.78% (3.125 μM) | 54.53% (6.25 μM) | 92.83% (12.5 μM) |
| Compound 5 | 23.27% | 40.28% | |
| Compound 6 | 20.41% | 35.98% | 33.80% |
| Compound 7 | 41.05% | 28.79% | 43.99% |
| Compound 8 | −1.83% | 17.41% | 6.10% |
| Compound 9 | 12.22% | 29.24% | 60.06% |
| Compound 10 | 10.82% | 25.32% | 45.93% |
| Compound 11 | 42.30% | 64.65% | |
| Compound 12 | 20.85% | 49.43% | 66.73% |
| Compound 13 | 18.05% | 42.38% | |
| Compound 14 | 17.02% | 43.19% | |
| Compound 15 | 26.47% | 48.24% | |
| Compound 16 | 31.39% | 46.75% | |
| Compound 17 | 26.34% | 53.97% | |

Example 19

Experimental results of compound 4 alleviating 3T3-L1 adipocytes lipolysis.

Glycerol assay was used to evaluate intracellular lipid content. Glycerol kinase phosphorylates glycerol to glycerol 3-phosphate; glycerol 3-phosphate is oxidized by glycerophosphate oxidase to produce hydrogen peroxide; the chromogenic substrate is converted to benzoquinone imine in the presence of peroxidase, and its optical density value is proportional to the glycerol concentration.

The above methods allow to evaluate the effect of drugs on the fat lipolysis cell model. The methods are as follows:

3T3-L1 cells were seeded in 6-well plates in a culture medium (high-glucose DMEM medium containing 10% FBS and 1% P/S) and placed in a 5% $CO_2$, 37° C. environment. The cells were allowed to grow to 100% confluence and continued to fuse for 3 days to start the differentiation operation. The culture medium for the first differentiation was high-glucose DMEM medium containing 0.5 mM IBMX, 5 mg/mL insulin, 1 μM dexamethasone and 10% FBS and 1% P/S, and then differentiated 3T3-L1 adipocytes for 72 h; The culture medium for the second differentiation was high-glucose DMEM medium containing 5 mg/mL insulin and 10% FBS, and 1% P/S, and then differentiated 3T3-L1 adipocytes for 72 h; the culture medium for the third differentiation was high-glucose DMEM medium containing 10% FBS, and 1% P/S, and then differentiated 3T3-L1 for 72 h; After successful differentiation, it was obvious that there were a large number of oil droplets in the cells. In addition, C26 cells were inoculated in T75 flasks in the culture medium (high-glucose DMEM medium containing 10% FBS, and 1% P/S) and placed in a 5% $CO_2$, 37° C. environment. While C26 cells ($6 \times 10^6$ cells/flask) were passaged, add 15 mL of phenol red-free high-glucose DMEM culture medium to the T75 flask with 100% confluent C26 cells and sequentially subculture for 48 h. To obtain the supernatant, centrifuge C26 culture medium at 1000 rpm for 3 min and at 4000 rpm for 10 min successively, and take the supernatant to obtain the C26 supernatant successively. The C26 supernatant was mixed with phenol red-free high-glucose DMEM medium at 1:1 ratio as a fat lipolysis-inducing medium. Except for the control group with phenol red-free high-glucose DMEM medium, the other each group was added with the same amount of fat lipolysis-inducing liquid; one group was used as the model group, and the rest groups were used as the experimental groups for drug administration. At the same time, compound 4 stock solution was also added into the cells at the following concentrations of 12.5 μM, 25 μM, 50 μM, 100 μM.

TABLE 3

Administration samples for adipocyte lipolysis in Example 19

| Ser. No. | No. | Test sample | component |
|---|---|---|---|
| 1 | CT (Control) | Control group | Phenol red free- high glucose DMEM culture medium |
| 2 | C26 medium | Model group | Phenol red free- high glucose DMEM culture medium + C26 medium |
| 3 | C26 + 4 (12.5 μM) | Experimental group 1 | Phenol red free- high glucose DMEM culture medium + C26 medium + 12.5 μM compound 4 |
| 4 | C26 + 4(25 μM) | Experimental group 2 | Phenol red free- high glucose DMEM culture medium + C26 medium + 25 μM compound 4 |
| 5 | C26 + 4(50 μM) | Experimental group 3 | Phenol red free- high glucose DMEM culture medium + C26 medium + 50 μM compound 4 |
| 6 | C26 + 4(100M) | Experimental group 4 | Phenol red free- high glucose DMEM culture medium + C26 medium + 100 μM compound 4 |

The glycerol detection method was performed as follows: after 48 h of action, the glycerol content in the supernatant was detected using the glycerol detection kit from Beijing Applygen Gene Technology Co., Ltd.

Results and Conclusions: Refer to the attached FIG. 47.

Figure 47:
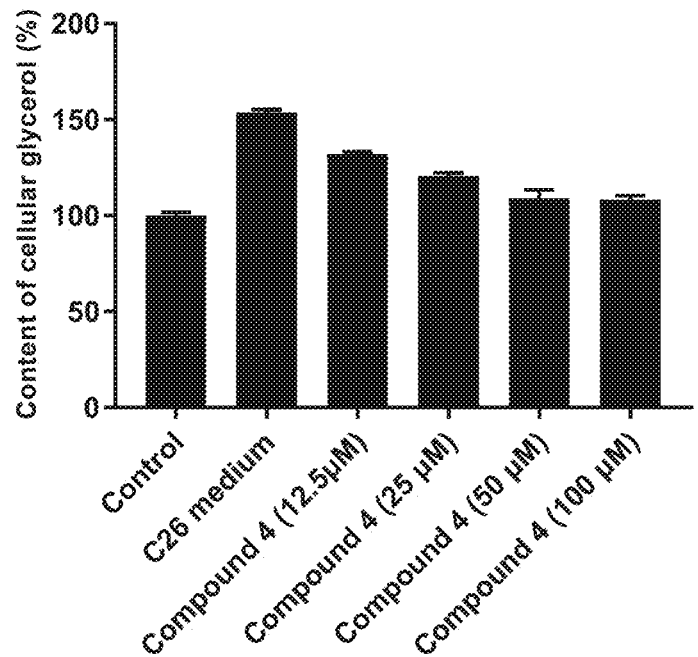
FIG. 47 shows the graph of the glycerol content test results of the experimental samples in Example 19.

The attached FIG. 47 shows the glycerol detection result of compound 4. As shown in FIG. 47, compound 4 showed a concentration-dependent reduction of glycerol released from 3T3-L1 mature adipocytes induced by C26 cell culture medium. The cellular glycerol contents of the control group, model group, experimental group 1, experimental group 2, experimental group 3 and experimental group 4 were 287.44 µM, 441.95 µM, 379.44 µM, 347.14 µM, 313.67 µM and 310.95 µM, respectively.

Example 20

The experimental results of cancer cachexia animal models treated with compound 4, by the following methods.

C26 cells were cultured in T75 culture flasks in the culture medium (RPMI-1640 medium containing 10% FBS, and P/S) and placed in a 5% $CO_2$, 37° C. environment. The cells were harvested by centrifugation at 1000 rpm for 3 min, and washed with ice-cold PBS buffer to remove the remaining culture medium and prepared into a cell suspension of $1\times10^7$ cells/mL. The cell suspension was inoculated into the left and right armpits of BALB/c mice with $1\times10^6$ cells/mouse for subsequent inoculation. When the tumor volume increased to about 800 cm3, the tumor was removed and homogenized at 3.5 mL of ice-old saline/g to obtain tumor tissue suspension. The mice to be inoculated were grouped according to their body weight, and the cell suspension was inoculated into the left armpit of BALB/c mice at the amount of 100 µL/mouse. The administration of the drug was started the day after inoculation. Compound 4 was first dissolved in DMSO and then mixed with pre-warmed PBS solution (37° C.) to form a homogeneous and stable solution at a final concentration of 1 mg/mL (3% DMSO+2% anhydrous ethanol+1% polyoxyethylene castor oil). The dose was 5 mg/kg and the route of administration was oral gavage (i.g). The body weight, body temperature, tumor size and food intake of the mice were monitored daily. The mice in the model group were considered to be in the advanced stage of cachexia when they were about 10% weight loss after 16 days. The muscle grip of mice's limbs was measured, and samples of gastrocnemius muscle, epididymal fat and tumor were obtained after the mice were executed by decolonization and the tissue samples were weighed.

The measurement method of the muscle grasping force is as follows: The researcher holds the mouse steadily with his right hand, puts the mouse on the "YLS-13A rat and mouse grasping force measuring instrument" to let the forelimbs of mouse firmly grasp the grasping plate and uses his left hand to stabilize the grasping plate. To measure the muscle grasping force of the mouse, the researcher slowly releases his left hand from the grasping plate and immediately uses his right hand to pull the mouse's tail backward slowly until the forelimbs are free from the grasping plate. Each mouse is repeated 8 times, and the average value of the 8 times is used as the skeletal muscle strength index of each mouse.

Results and Conclusions: Referring to FIGS. 48 to 58, the three curves in the figures represent the healthy group, the C26 tumor model group and the dosing group (compound 4 group, where compound 4 was administrated at a dose of 5 mg/kg), respectively.

Figure 48:
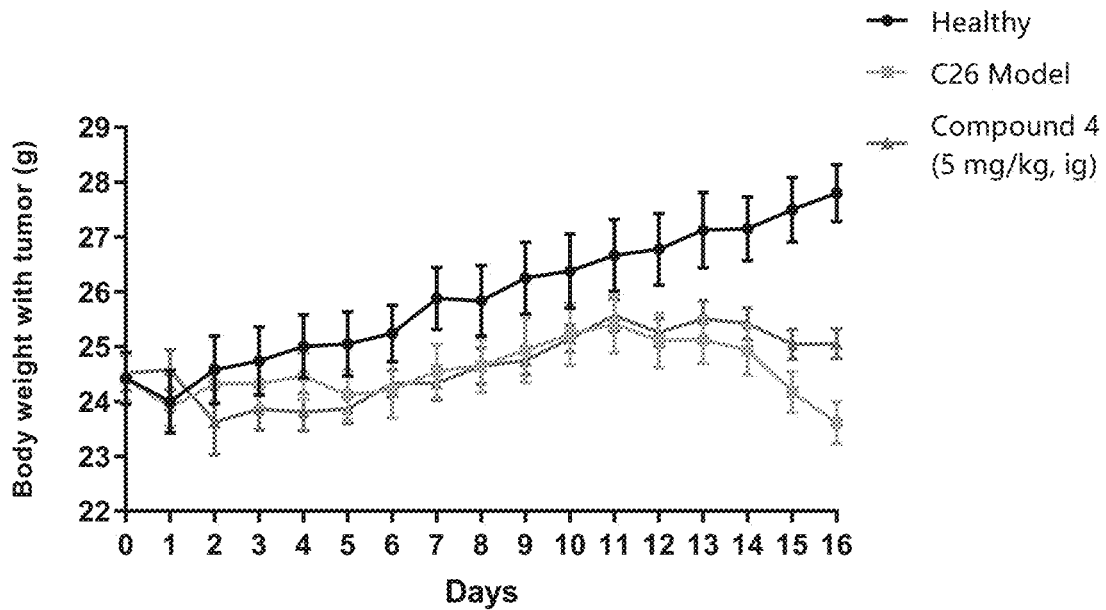
FIG. 48 shows the change curve of body weight of the tumor-bearing mice in Example 20.
Figure 49:
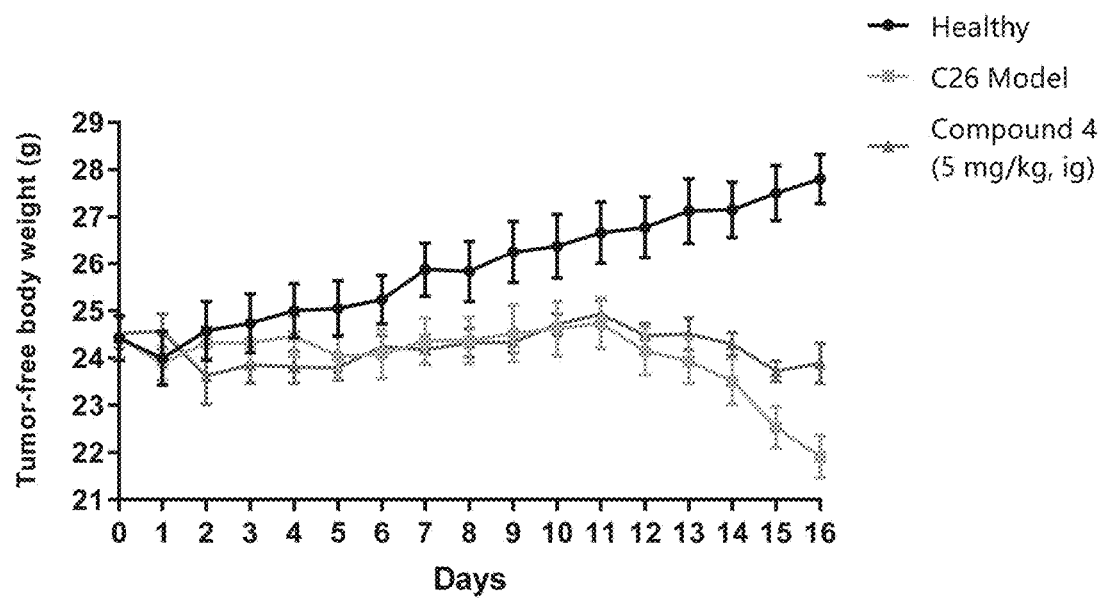
FIG. 49 shows the change curve of body weight of the tumor-free mice in Example 20.
Figure 50:
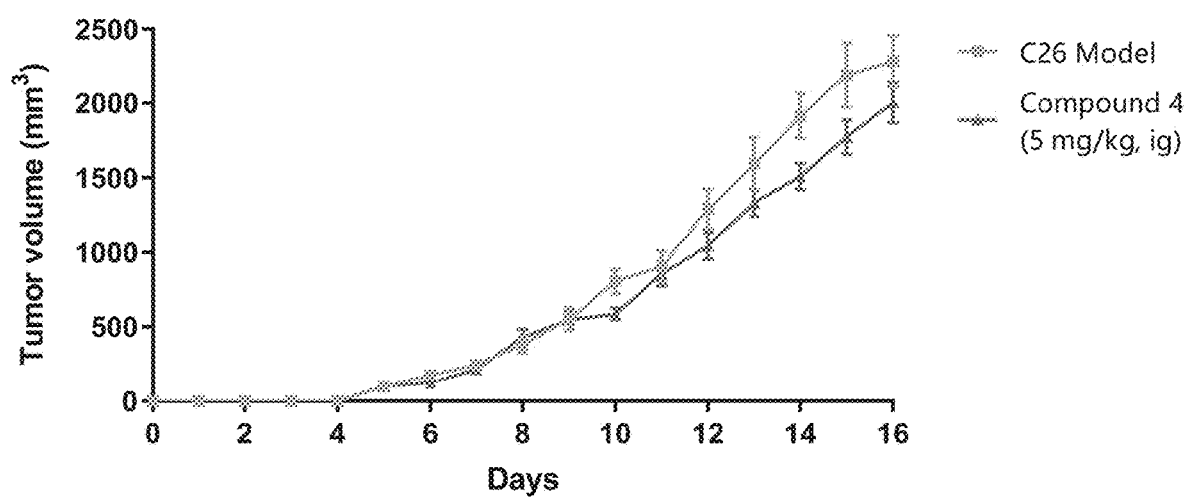
FIG. 50 is the tumor volume change curve of the mice in Example 20.
Figure 51:
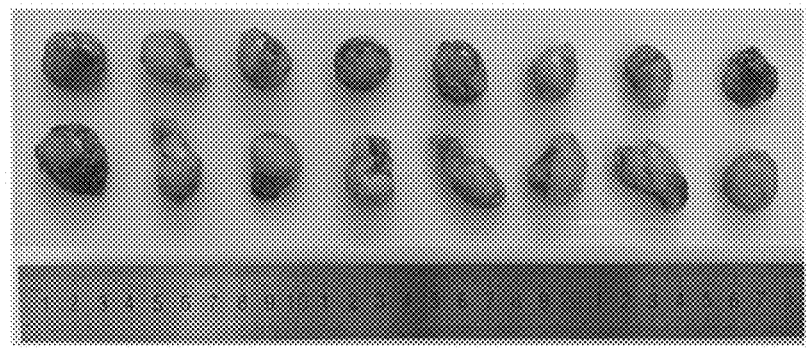
FIG. 51 shows the real photograph of tumors of the mice in Example 20.

The attached FIGS. 48 to 51 show the body weight with tumors (FIG. 48), the body weight without tumors (FIG. 49), the tumor volume (FIG. 50) and the real tumor photos (FIG. 51) during the survival period of the mice, in which the body weight with tumors and the body weight without tumors are the average weight of 8 mice, and the tumor volume is the average volume of the tumors of 8 mice, and the real tumor photos are the real photos of the tumors of 8 mice. As shown in FIG. 48, the body weight of mice in the healthy group continued to increase, while the body weight of the tumor-bearing mice in the C26 tumor model group stated to decrease from the beginning to the 11th day of the experiment, and continued to decrease until the end of the experiment. As shown in attached FIG. 49, the same was true for the body weight without tumors, while the compound 4 group can significantly alleviate the weight loss of the mice and by the end of the experiment, both the body weight with tumor and the body weight without tumor were higher than those in the C26 tumor model group, and the difference was statistically significant (p<0.01). However, as shown in FIGS. 50 and 51, the tumor volume was slightly reduced in the compound 4 group compared with the C26 tumor model group, but the difference was not significant, indicating that the compound 4 had no significant inhibitory effect on growth of C26 tumors.

Figure 52:
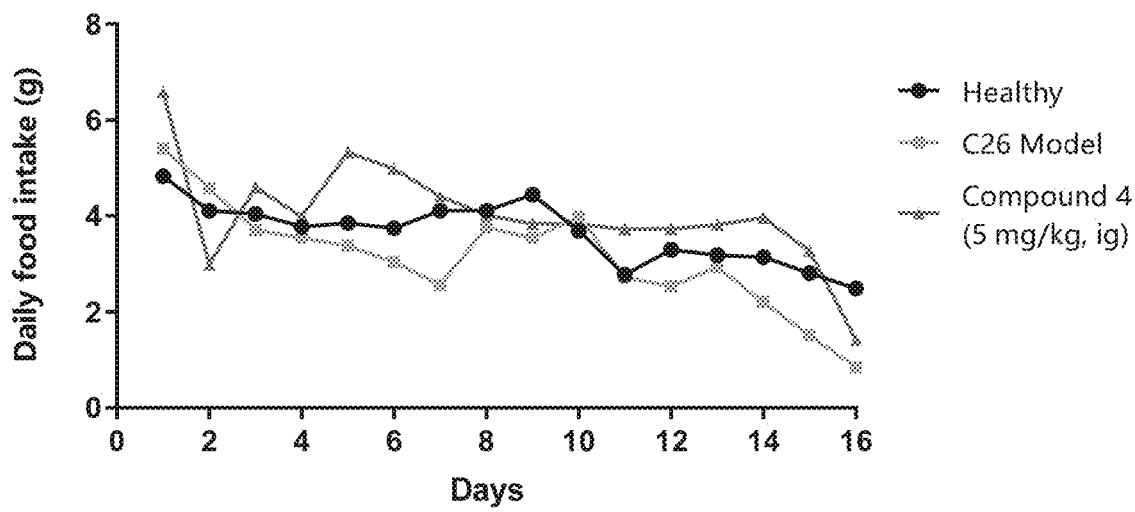
FIG. 52 shows the change curve of the average daily food intake of the mice in Example 20.
Figure 53:
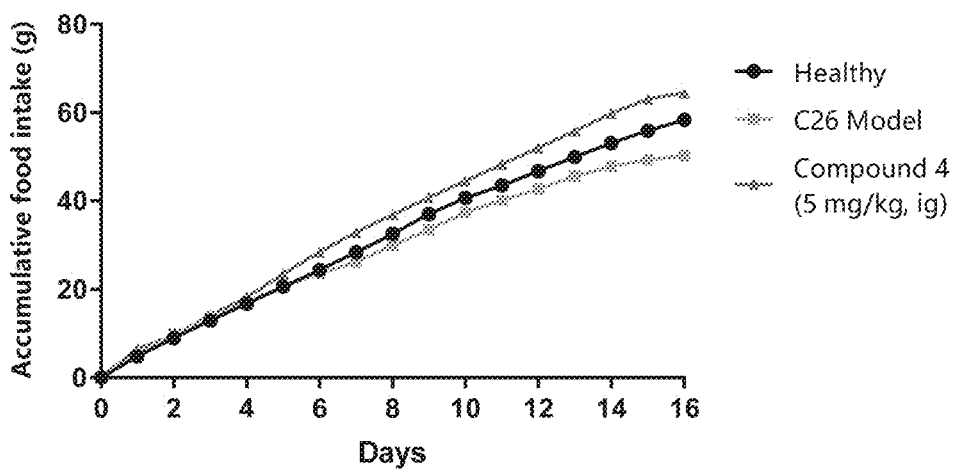
FIG. 53 shows the change curve of the average accumulative food intake of the mice in Example 20.

The average daily food intake and the average accumulative food intake during the survival period of mice are shown in FIG. 52 to 53, which are the average calculation results of 8 mice. The mice in the C26 tumor model group showed significant decrease in food intake compared to the healthy group. The compound 4 group showed higher food intake than the C26 tumor model group, suggesting that it improved appetite.

Figure 54:
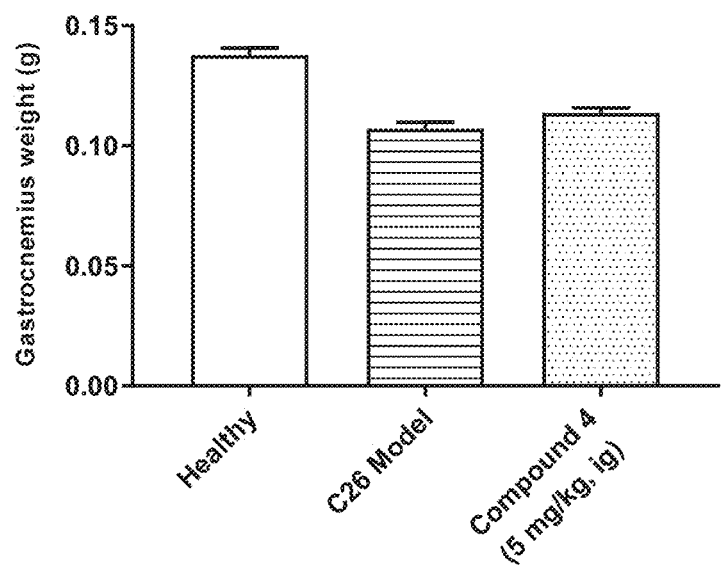
FIG. 54 shows the graph of the gastrocnemius muscle mass measurement results of mice in Example 20.
Figure 55:
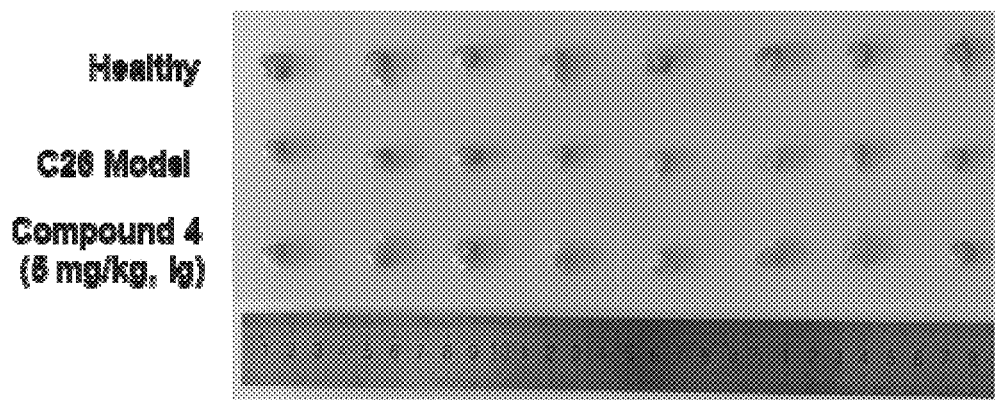
FIG. 55 shows the real photograph of the gastrocnemius muscle of the mice in Example 20.
Figure 56:
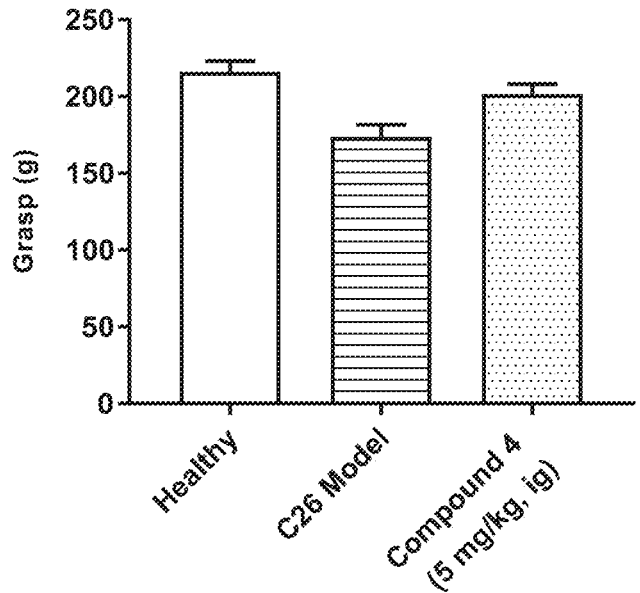
FIG. 56 shows the graph of grasping force test results of the mice's muscle in Example 20.

The attached FIGS. 54 to 55 show the mass of the gastrocnemius muscle in mice and the real pictures of the gastrocnemius muscle, and the gastrocnemius muscle mass is the average value of 8 mice, and the real pictures of the gastrocnemius muscle is the result of 8 mice/group. As shown in FIGS. 54 and 55, the gastrocnemius muscle mass of mice in the C26 tumor model group was significantly lighter than that in the healthy group, and the difference was statistically significant (p<0.001). Compound 4 could significantly alleviate gastrocnemius muscle atrophy (p<0.05). FIG. 56 shows the muscle grasping force of the mice's limbs. The muscle grasping force of the mice in the C26 tumor model group was significantly lower than that of the healthy group and the compound 4 group, and the difference was statistically significant (p<0.001). Compound 4 could significantly enhance the muscle grasping force (p<0.05).

Figure 57:
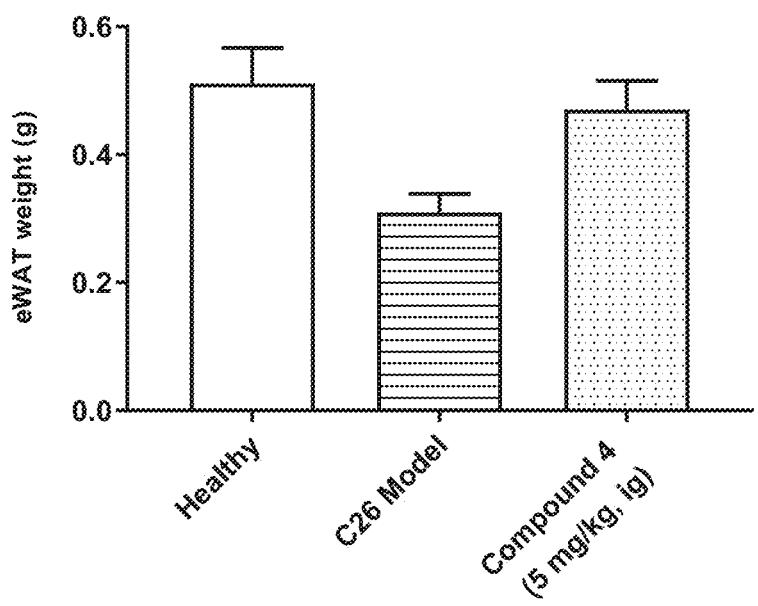
FIG. 57 shows the graph of the epididymal fat mass measurement results in mice in Example 20.
Figure 58:
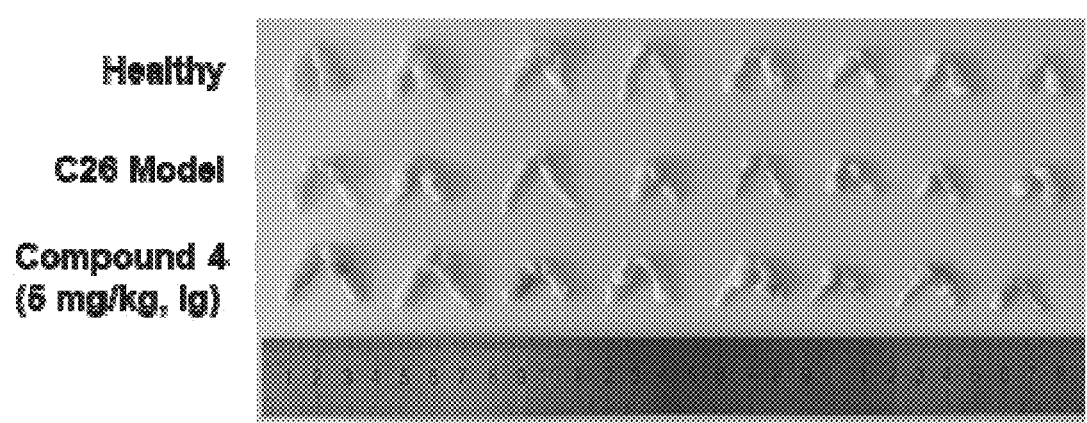
FIG. 58 shows the real photograph of the epididymal fat of mice in Example 20.

The attached FIGS. 57 to 58 show the epididymal fat mass of mice with real pictures of epididymal fat. As shown in the figure, the epididymal fat mass of mice in the C26 tumor model group was significantly lighter than that in the healthy group and compound 4 group, and the difference was statistically significant (p<0.01). Compound 4 could significantly increase the epididymal fat mass (p<0.05).

The above results suggest that compound 4 could alleviate the weight loss, muscle atrophy, fat degradation and body temperature decrease caused by cancer cachexia and improve appetite without affecting the tumor size.

The above described is a preferred embodiment of the present invention and it should be noted that, for those researchers of ordinary skill in the technical field covered by the present invention, several supplements and improvements can be made without departing from the method of the present invention, and these supplements and improvements should also be considered as the protection scope of the present invention.

What is claimed is:

1. A carbamo (dithioperoxo) thioate compound of formula I:

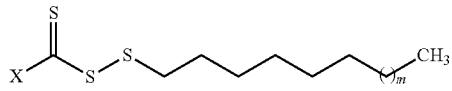

or its pharmaceutically acceptable salt thereof, wherein, m=1-11, X is a nitrogen-containing aliphatic heterocycle and the nitrogen atom in the aliphatic heterocycle is connected to the carbon atom of the thiocarbonyl group, wherein the nitrogen-containing aliphatic heterocycle is selected from pyrrolidine, morpholine, piperazine, indoline, isoindolin, octahydro-1H-indole, octahydro-1H-isoindole, azetidine and 2-oxa-6-azaspiro[3.4]octane.

2. The carbamo (dithioperoxo) thioate compound or its pharmaceutically acceptable salt according to claim 1, wherein, m=3-5.

3. The carbamo (dithioperoxo) thioate compound or its pharmaceutically acceptable salt according to claim 1, wherein m=5.

4. The carbamo (dithioperoxo) thioate compound or its pharmaceutically acceptable salt according to claim 1, wherein the nitrogen-containing aliphatic heterocycle is pyrrolidine.

5. The carbamo (dithioperoxo) thioate compound or its pharmaceutically acceptable salt according with to claim 1, wherein said compound is selected from the following compounds:

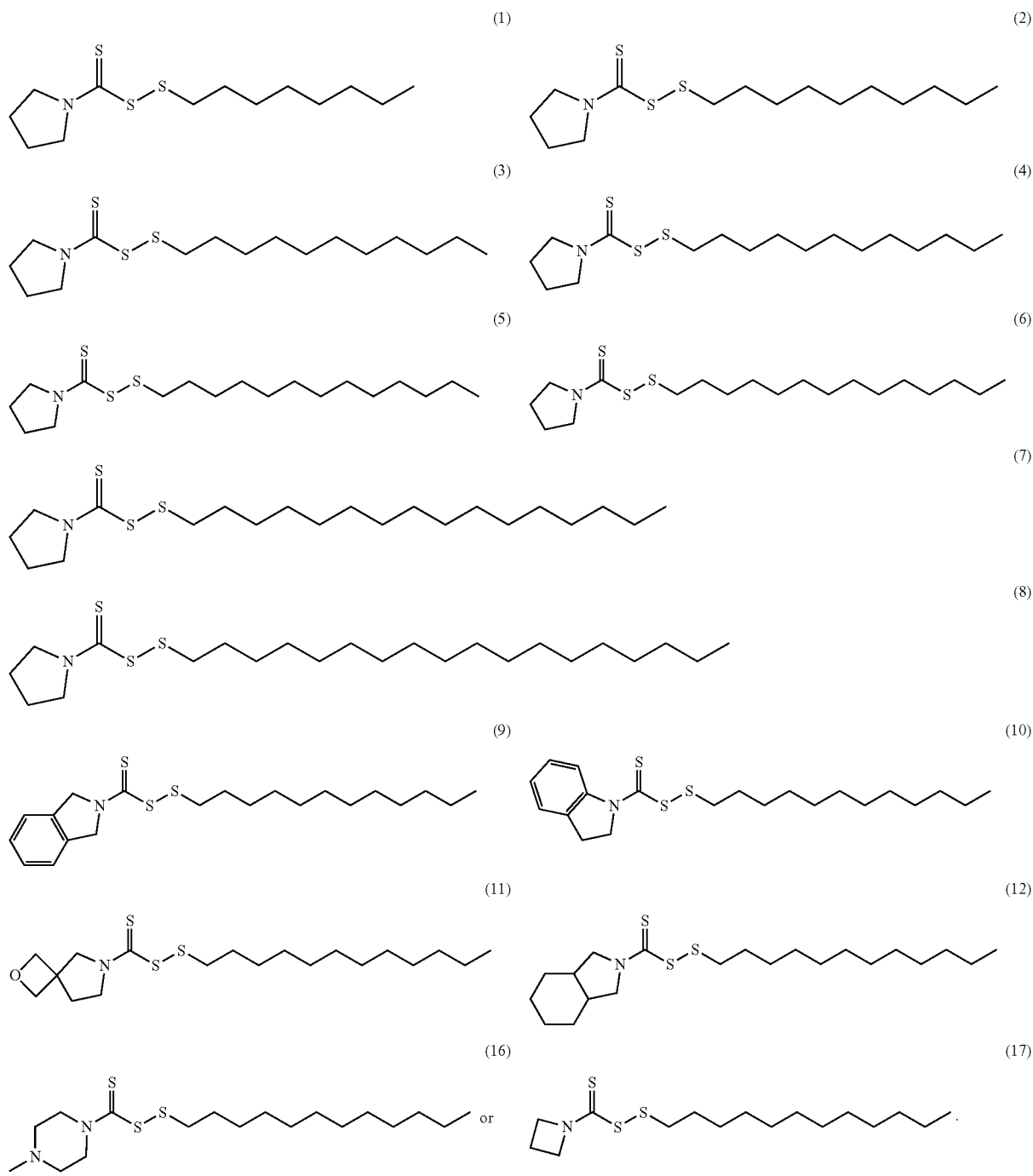

6. A pharmaceutical composition, comprising the carbamo (dithioperoxo) thioate compound or its pharmaceutically acceptable salt according to claim 1, and its a pharmaceutically acceptable additive.

7. A method of treating cachexia, comprising administering the carbamo (dithioperoxo) thioate compound or its pharmaceutically acceptable salt according to claim 1 to a subject.

8. The method according to claim 7, wherein the cachexia is cancer cachexia.

* * * * *